United States Patent
Takagi et al.

(10) Patent No.: US 9,656,042 B2
(45) Date of Patent: May 23, 2017

(54) CATHETER AND METHOD

(71) Applicant: Terumo Kabushiki Kaisha, Tokyo (JP)

(72) Inventors: Ayumu Takagi, Tustin, CA (US);
Katsunori Ebata, Kanagawa (JP);
Ryusuke Takashige, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 419 days.

(21) Appl. No.: 13/728,437

(22) Filed: Dec. 27, 2012

(65) Prior Publication Data

US 2013/0116651 A1     May 9, 2013

Related U.S. Application Data

(63) Continuation of application No. PCT/JP2011/064623, filed on Jun. 27, 2011.

(30) Foreign Application Priority Data

Jun. 30, 2010 (JP) ................................ 2010-148744
Jun. 30, 2010 (JP) ................................ 2010-148746
Jun. 30, 2010 (JP) ................................ 2010-148747

(51) Int. Cl.
*A61M 25/00*     (2006.01)
*A61M 39/10*     (2006.01)

(52) U.S. Cl.
CPC .... *A61M 25/0054* (2013.01); *A61M 25/0097* (2013.01); *A61M 2025/0098* (2013.01); *A61M 2039/1066* (2013.01)

(58) Field of Classification Search
CPC .................. A61M 2025/0098; A61M 25/0097
See application file for complete search history.

(56) References Cited

U.S. PATENT DOCUMENTS

| | | | | |
|---|---|---|---|---|
| 2,189,987 A | * | 2/1940 | Kellems | 439/447 |
| 2,219,326 A | * | 10/1940 | Meuer | 439/448 |
| 3,487,160 A | * | 12/1969 | Johnsen | 174/88 R |
| 3,618,613 A | * | 11/1971 | Schulte | 604/523 |
| 4,509,877 A | | 4/1985 | Sobin et al. | |
| 4,511,163 A | * | 4/1985 | Harris et al. | 285/148.16 |

(Continued)

FOREIGN PATENT DOCUMENTS

| | | |
|---|---|---|
| EP | 1 010 439 A1 | 6/2000 |
| JP | 2004-524107 A | 8/2004 |

(Continued)

OTHER PUBLICATIONS

The Chinese Office Action for the related Chinese Patent Application No. 201180032040.9 dated Mar. 31, 2014.

(Continued)

*Primary Examiner* — Scott Medway
(74) *Attorney, Agent, or Firm* — Kenealy Vaidya LLP

(57) ABSTRACT

The presently disclosed subject matter relates to a catheter and method. The catheter can be configured as a guiding catheter with a flexible shaft section, a hub disposed at a proximal portion of the shaft section, and a strain relief section that surrounds a predetermined proximal-side range of the shaft section. A distal end of the strain relief section can be moved along an axial direction of the shaft section at least toward the side where the hub is located.

10 Claims, 27 Drawing Sheets

(56) References Cited

U.S. PATENT DOCUMENTS

| | | | |
|---|---|---|---|
| 4,602,808 A * | 7/1986 | Herron et al. | 285/45 |
| 4,610,674 A * | 9/1986 | Suzuki et al. | 604/528 |
| 4,875,481 A * | 10/1989 | Higgins | 606/194 |
| 5,076,656 A * | 12/1991 | Briggs et al. | 385/71 |
| 5,094,552 A | 3/1992 | Monroe et al. | |
| 5,095,915 A * | 3/1992 | Engelson | 600/585 |
| 5,181,750 A * | 1/1993 | Reum | 285/38 |
| 5,380,301 A * | 1/1995 | Prichard et al. | 604/533 |
| 5,466,230 A | 11/1995 | Davila | |
| 5,542,432 A * | 8/1996 | Slater et al. | 600/564 |
| 5,545,151 A * | 8/1996 | O'Connor et al. | 604/524 |
| 5,558,652 A * | 9/1996 | Henke | 604/529 |
| 5,582,212 A * | 12/1996 | Tanzosh | 138/110 |
| 5,638,827 A * | 6/1997 | Palmer et al. | 600/564 |
| 5,725,513 A * | 3/1998 | Ju et al. | 604/527 |
| 5,951,539 A * | 9/1999 | Nita et al. | 604/526 |
| 6,068,622 A | 5/2000 | Sater et al. | |
| 6,228,073 B1 * | 5/2001 | Noone et al. | 604/533 |
| 6,273,404 B1 | 8/2001 | Holman et al. | |
| 6,283,950 B1 | 9/2001 | Appling | |
| 6,500,285 B2 * | 12/2002 | Pepin et al. | 156/86 |
| 7,214,220 B2 * | 5/2007 | McGlinch et al. | 604/533 |
| 7,625,365 B2 * | 12/2009 | McGlinch et al. | 604/533 |
| 8,012,144 B2 * | 9/2011 | Moberg | 604/533 |
| 8,435,216 B2 * | 5/2013 | Spinoza | 604/174 |
| 8,784,379 B2 * | 7/2014 | Akitomo | 604/117 |
| 8,992,415 B2 * | 3/2015 | Deuel et al. | 600/37 |
| 2001/0020161 A1 * | 9/2001 | Klima et al. | 604/524 |
| 2001/0049519 A1 | 12/2001 | Holman et al. | |
| 2003/0060803 A1 | 3/2003 | McGlinch et al. | |
| 2005/0096688 A1 | 5/2005 | Slazas et al. | |
| 2005/0107739 A1 | 5/2005 | Palma | |
| 2006/0064159 A1 | 3/2006 | Porter et al. | |
| 2006/0264904 A1 * | 11/2006 | Kerby et al. | 604/523 |
| 2008/0147001 A1 * | 6/2008 | Al-Marashi et al. | 604/103.04 |
| 2011/0306826 A1 * | 12/2011 | Franklin et al. | 600/37 |
| 2013/0150807 A1 * | 6/2013 | Hamuro et al. | 604/264 |
| 2014/0207069 A1 * | 7/2014 | Bierman et al. | 604/167.03 |
| 2015/0011977 A1 * | 1/2015 | Kuniyasu | 604/507 |

FOREIGN PATENT DOCUMENTS

| | | |
|---|---|---|
| JP | 2005-532833 A | 11/2005 |
| JP | 2008-511414 A | 4/2008 |
| JP | 2008-539962 A | 11/2008 |
| WO | 02/074366 A2 | 9/2002 |
| WO | 03/026535 A2 | 4/2003 |
| WO | WO2006/026687 A2 | 3/2006 |
| WO | WO2006/122155 A1 | 11/2006 |

OTHER PUBLICATIONS

The extended European Search Report for the related European Patent Application No. 11800763.2 dated Feb. 10, 2014.
Office Action from Japanese Patent App. No. 2012-522609 (Jun. 9, 2015).
Japanese Office Action from the related Japanese Patent App. No. 2012-522609 dated Dec. 15, 2015.
International Search Report for PCT/JP2011/064623 dated Jul. 26, 2011.

* cited by examiner

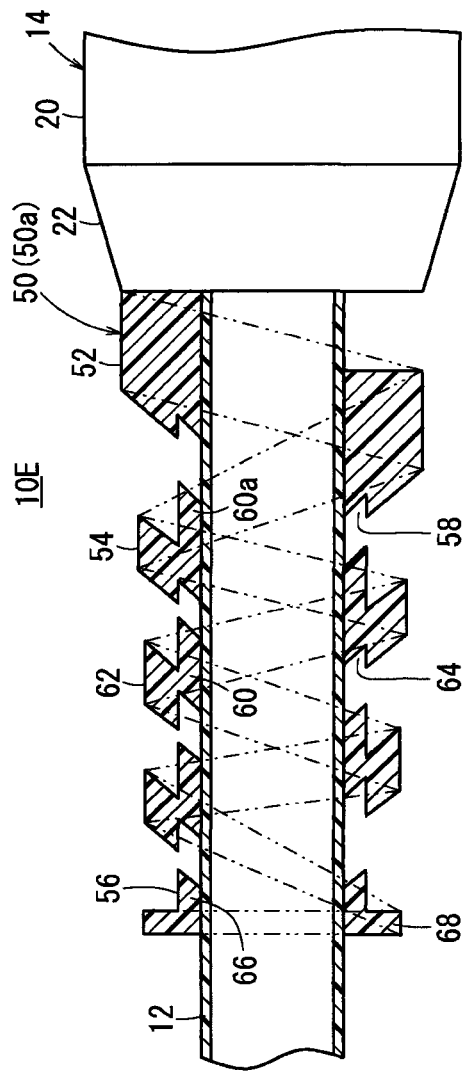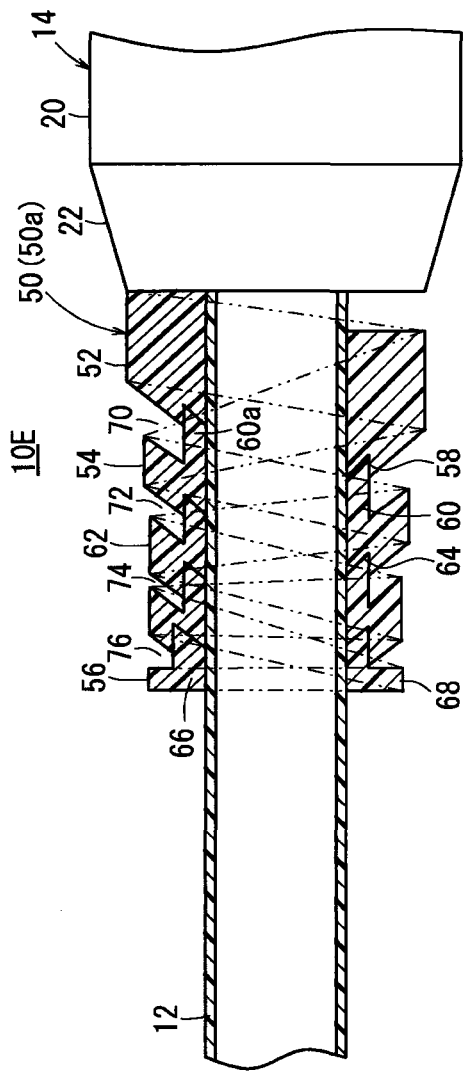
FIG. 6A
FIG. 6B

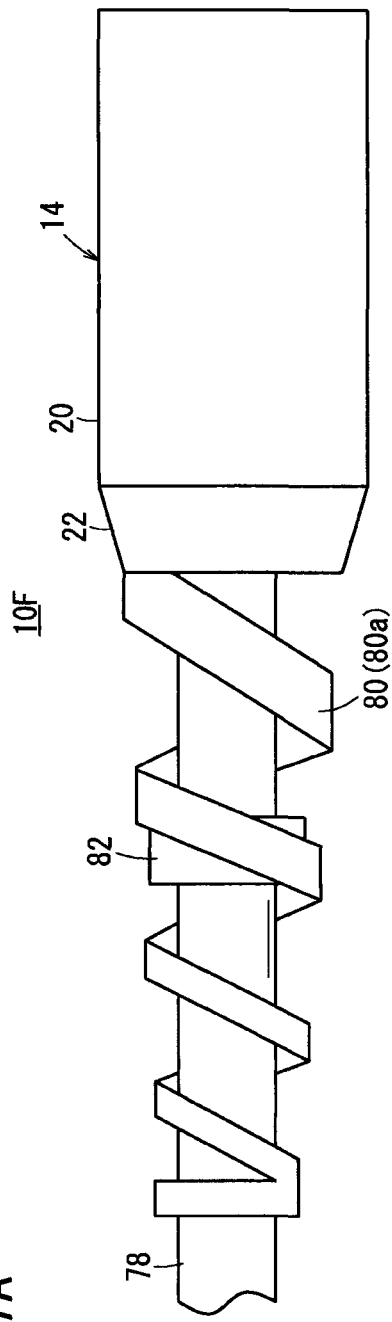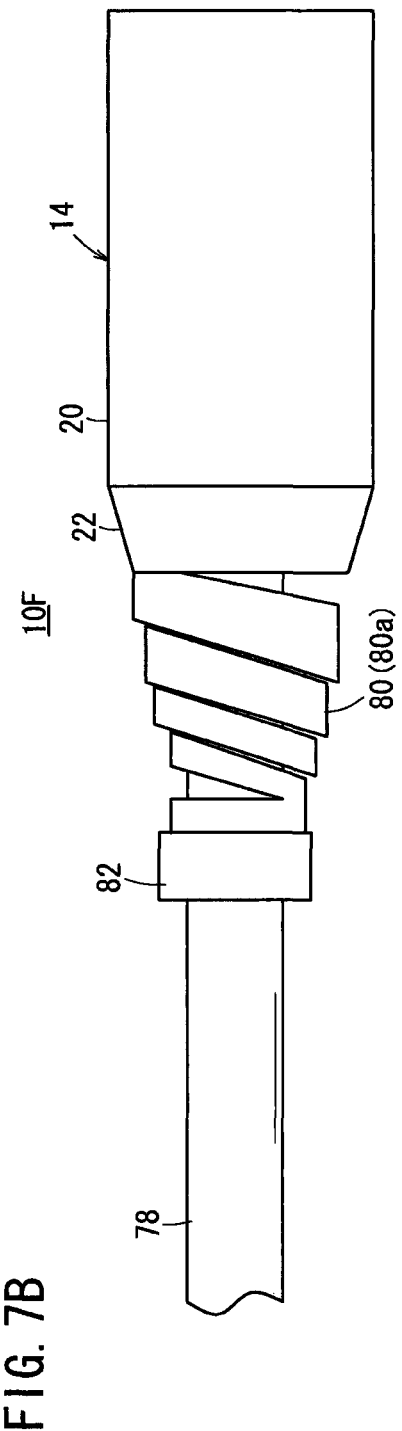
FIG. 7A
FIG. 7B

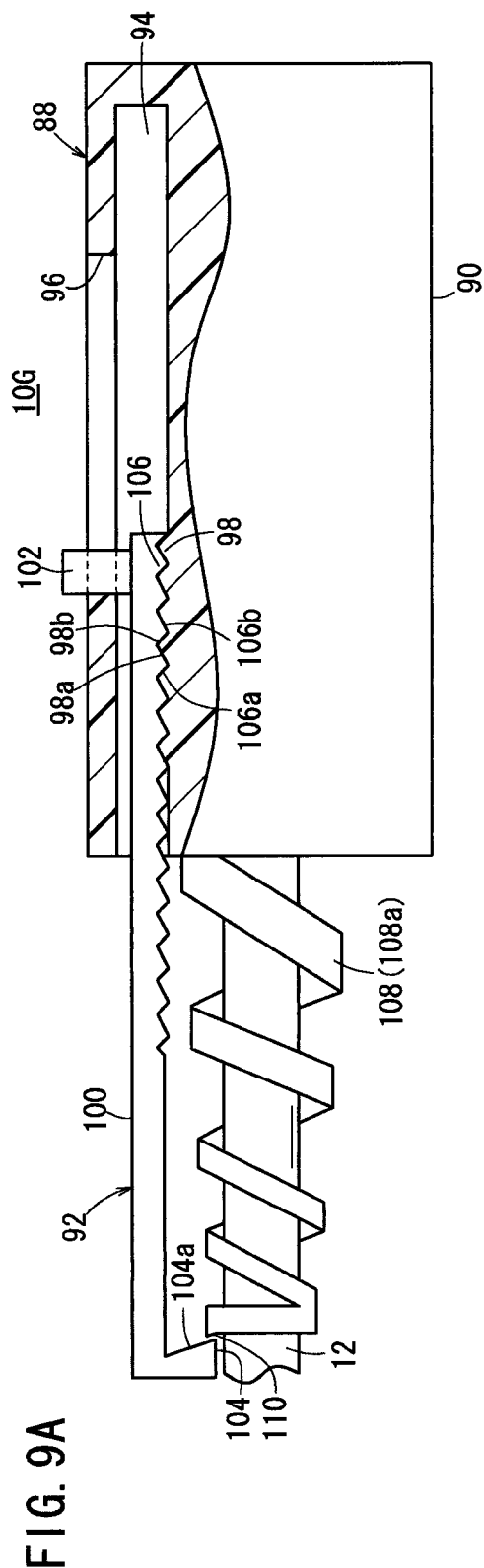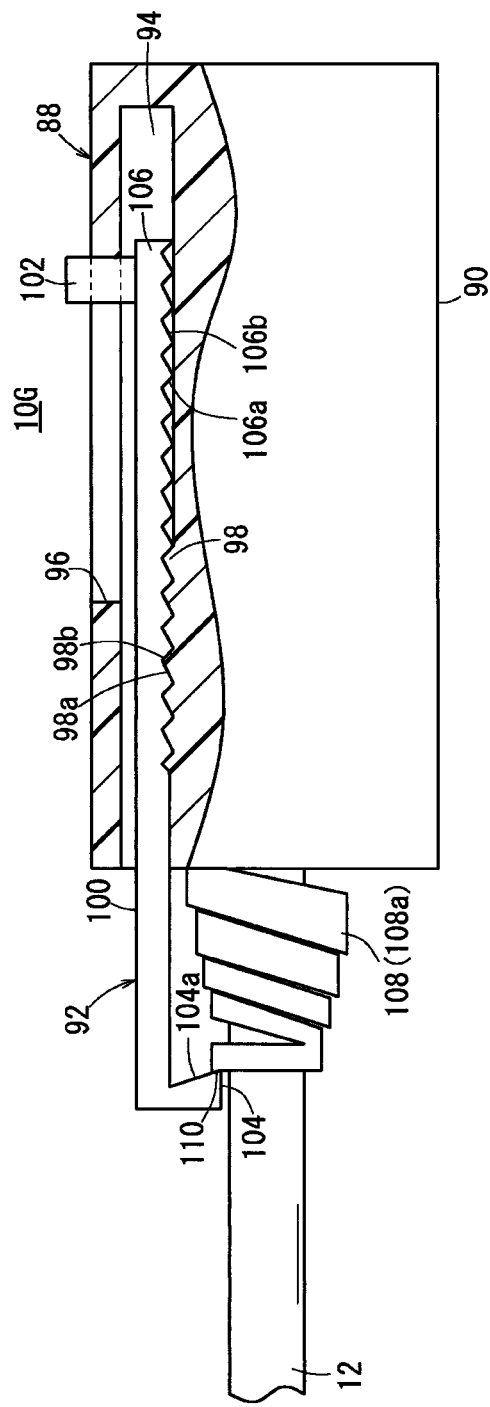

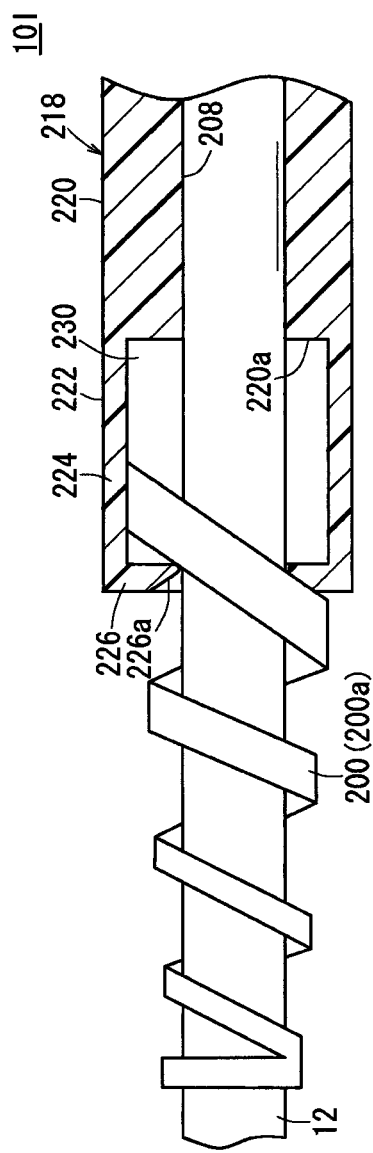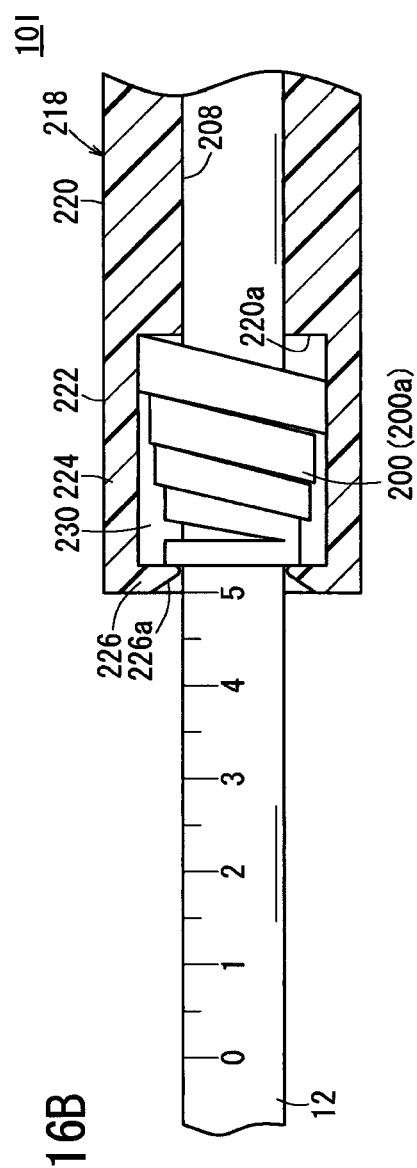
FIG. 16A
FIG. 16B

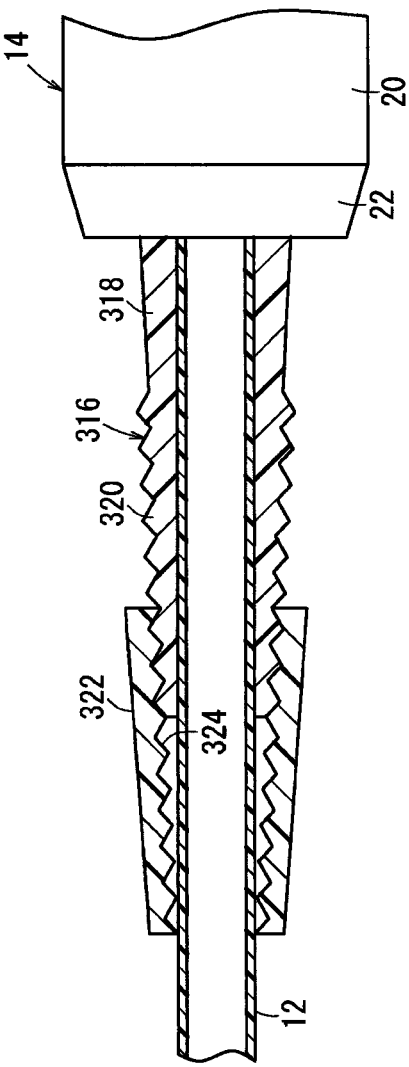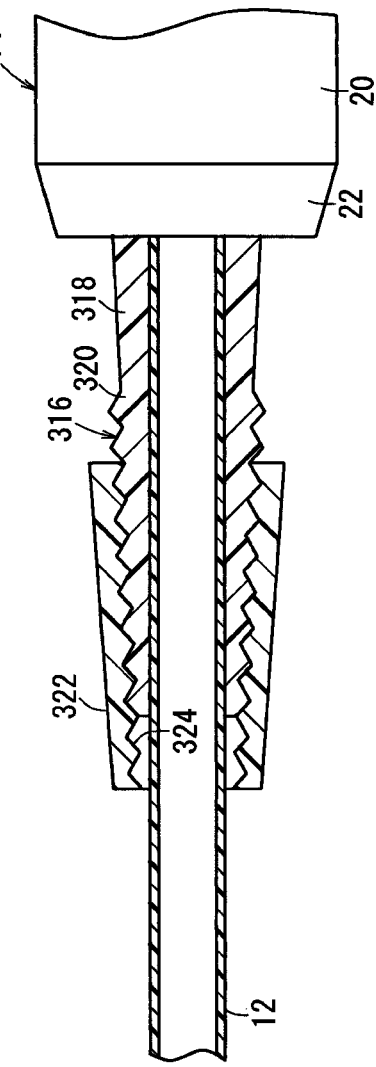
FIG. 22A
FIG. 22B

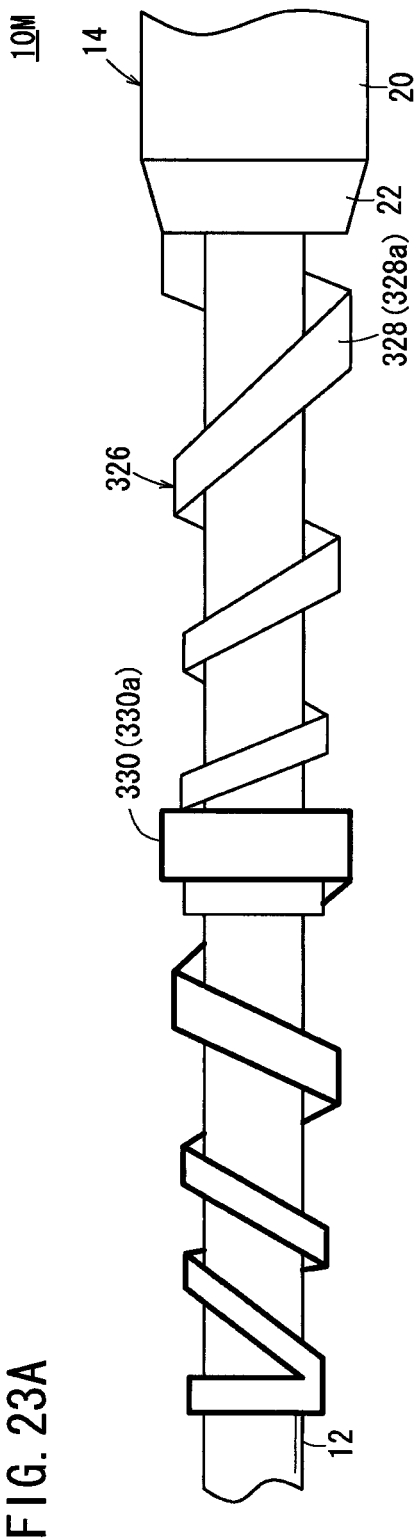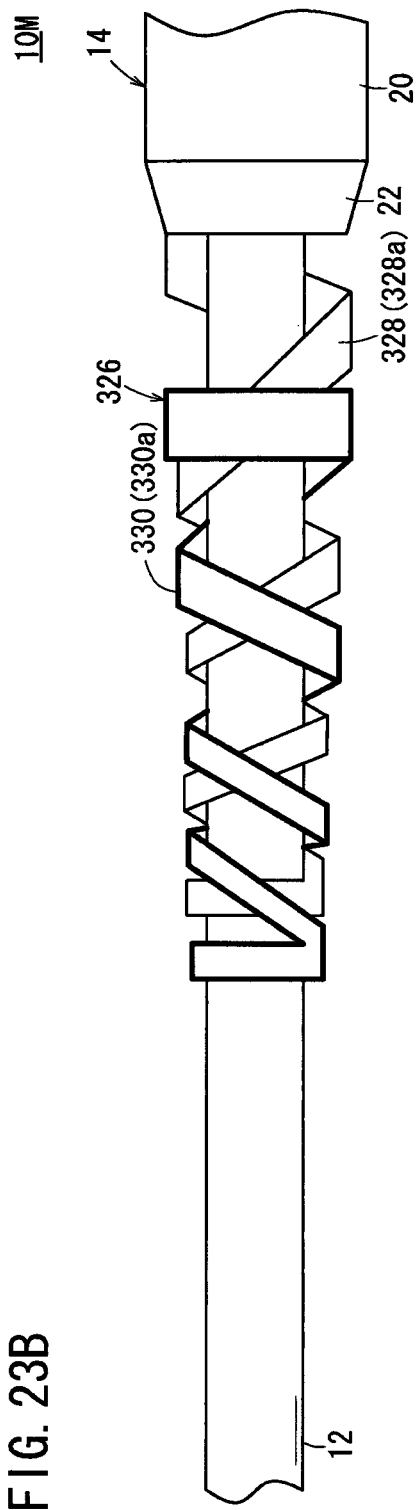
FIG. 23A
FIG. 23B

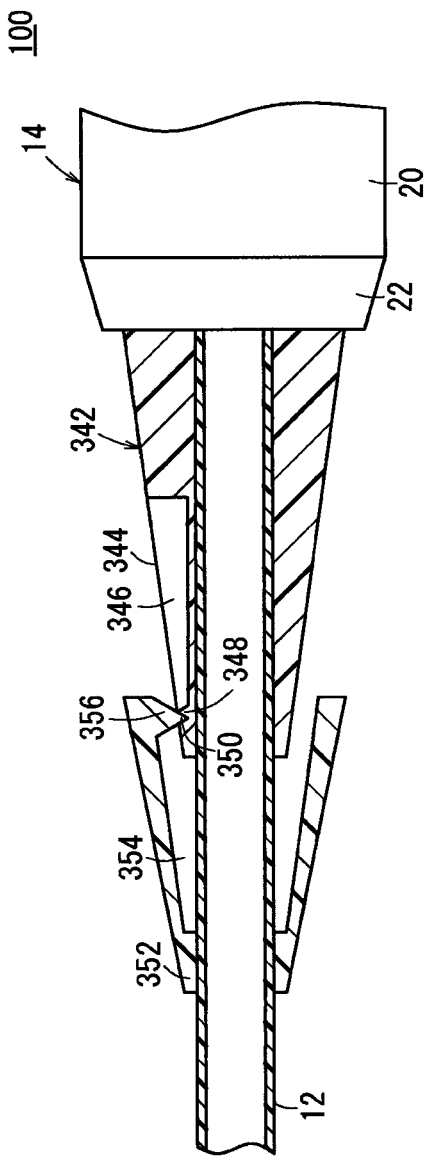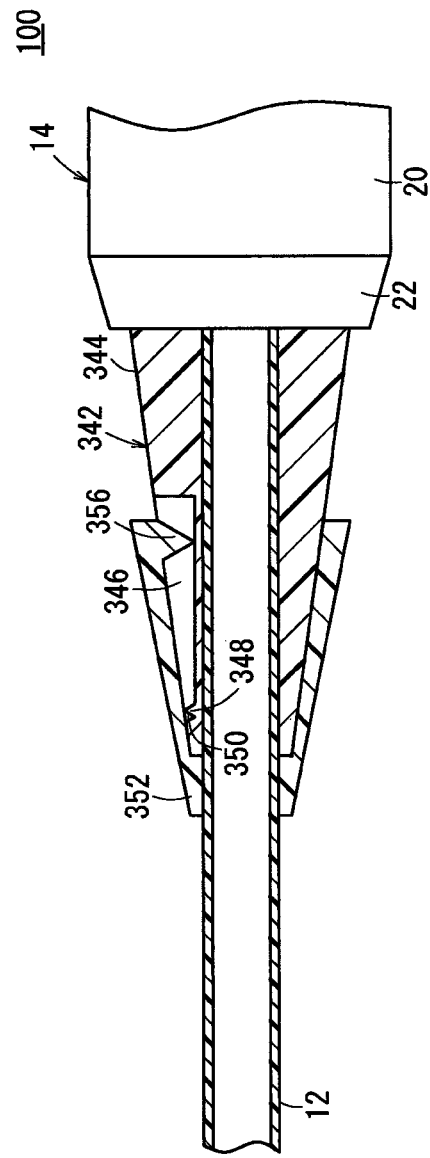

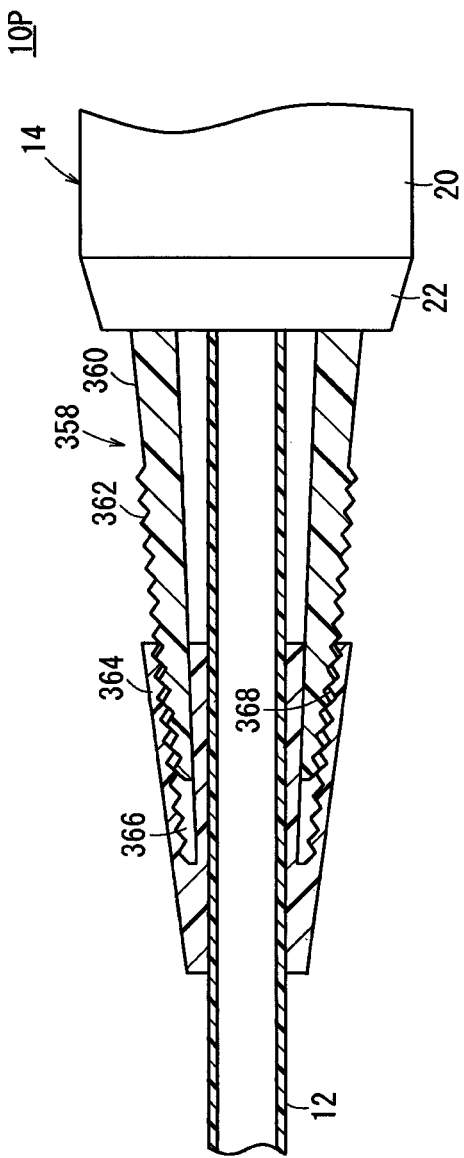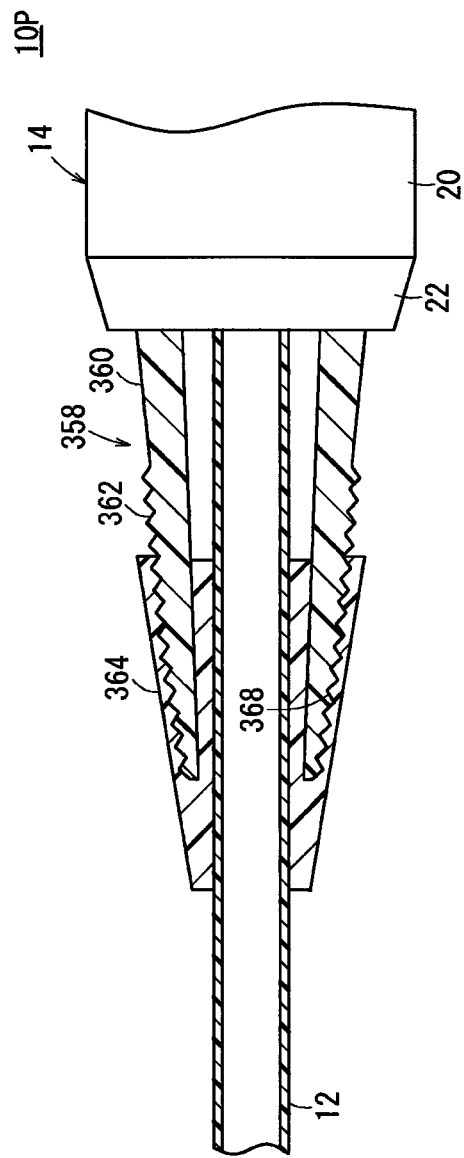

CATHETER AND METHOD

This application is a PCT Bypass Continuation of PCT Application No. PCT/JP2011/064623, filed Jun. 27, 2011, and hereby claims priority under 35 U.S.C. §119 to Japanese patent application nos. 2010-148747; 2010-148746 and 2010-148744, all filed Jun. 30, 2010, the entireties of all of which are incorporated herein by reference.

TECHNICAL FIELD

The presently disclosed subject matter relates to a catheter provided with a strain relief section which is disposed at a distal end of a hub and which surrounds a predetermined proximal-side range of a shaft section.

BACKGROUND ART

Conventionally, a procedure for introducing a catheter into a living organ such as a blood vessel and treating a lesion part (for example, a stenosed part) in the living organ has been widely practiced.

As this type of catheter, a technical thought has been proposed wherein a hub is connected to a proximal portion of a long catheter body (shaft section), and a strain relief section disposed at a distal end of the hub is fixed to a predetermined proximal-side range of the shaft section, whereby an anti-kinking property is exhibited at a proximal-side portion of the shaft section (see U.S. Pat. No. 6,068,622 and U.S. Published Application No. 2001/0049519).

SUMMARY

In the treatment of cardiac infarction or stenocardia, a procedure can be conducted in which a shaft section of a guiding catheter is inserted into a blood vessel through an insertion instrument, and a distal end of the shaft section is disposed at a desired position in a living organ (for example, the vicinity of a stenosed part, or an entrance of a coronary artery, a carotid artery, a renal artery or the like).

However, there are individual differences in the blood vessel shape (e.g., a manner of meandering) or blood vessel length. Therefore, the device disclosed in the above-mentioned U.S. Pat. No. 6,068,622 or U.S. Published Application No. 2001/0049519 has problems which can be summarized as follows. Since the distance from the distal end of the shaft section to a distal end of the strain relief section (an effective length of the shaft section) is constant, it may be impossible to bring the distal end of the shaft section to a desired position in a living organ, in cases where the length of the blood vessel from the insertion instrument (a position of insertion of the shaft section into a living body) to the desired position in the living organ is comparatively large.

For coping with such a problem, it may be contemplated to preliminarily set the effective length of the shaft section to a large value. In this case, however, the overall length of the catheter is also enlarged and, therefore, operability of the catheter can be diminished. In addition, the length of a medical instrument inserted into the catheter may become insufficient. Incidentally, if the strain relief section is omitted so as to enlarge the effective length of the shaft section, it becomes difficult and/or impossible to obtain the anti-kinking property at the proximal-side portion of the shaft section.

The presently disclosed subject matter has been made in consideration of the above-mentioned problems and other considerations. The presently disclosed subject matter includes a catheter capable of exhibiting anti-kinking properties at the proximal-side portion of the shaft section, being excellent in operability, and capable of coping with individual differences in the shape of the blood vessel into the shaft section is inserted, including the meandering shape of the blood vessel, the length of the blood vessel, etc.

According to an aspect of the presently disclosed subject matter a catheter can include: a flexible shaft section; a hub disposed at a proximal portion of the shaft section; and a strain relief section surrounding a predetermined proximal-side range of the shaft section, characterized in that a distal end of the strain relief section can be displaced along an axial direction of the shaft section at least toward the side where the hub is located.

According to another aspect of the presently disclosed subject matter, the effective length of the shaft section can be enlarged by displacing the distal end of the strain relief section toward the side where the hub is located. Therefore, even in the cases where the blood vessel from an insertion instrument to a desired position in a living organ is comparatively long or meandering, it is possible to enlarge the effective length of the shaft section and thereby to bring the distal end of the shaft section to the desired position in the living organ. In this case, the strain relief section is not omitted and, therefore, an anti-kinking property can be exhibited at a proximal-side portion of the shaft section. In addition, since the overall length of the catheter is not enlarged, excellent operability of the catheter can be maintained.

According to another aspect of the presently disclosed subject matter the strain relief section may be at least contractible in the axial direction of the shaft section.

According to another aspect of the presently disclosed subject matter, the effective length of the shaft section can be enlarged by contracting the strain relief section.

According to another aspect of the presently disclosed subject matter the strain relief section may be formed in a belt-like shape and be spirally wound around the shaft section.

According to another aspect of the presently disclosed subject matter, the strain relief section is spirally wound, so that the strain relief section can be easily contracted by regulating (narrowing) the interval between adjacent spiral turns of the belt.

According to another aspect of the presently disclosed subject matter at least either one of an outer circumferential surface and an inner circumferential surface of the strain relief section may be formed with a groove.

According to another aspect of the presently disclosed subject matter, when the strain relief section is contracted, that part of the strain relief section which constitutes the groove can be bent suitably. Therefore, the anti-kinking property can be suitably exhibited at the proximal-side portion of the shaft section.

According to another aspect of the presently disclosed subject matter the hub may be formed with a storage chamber in which at least part of the strain relief section can be stored.

According to another aspect of the presently disclosed subject matter the effective length of the shaft section can be enlarged by storing at least part of the strain relief section into the storage chamber.

According to another aspect of the presently disclosed subject matter the strain relief section may be spirally wound around the shaft section, and the storage chamber may be formed with a spiral groove capable of engagement with the strain relief section.

According to another aspect of the presently disclosed subject matter, by relatively rotating the hub and the strain relief section, the strain relief section can be advanced into the storage chamber while in engagement with the spiral groove. In addition, the amount of enlargement of the effective length of the shaft section can be set arbitrarily, by regulating the amount of rotation of the strain relief section.

According to another aspect of the presently disclosed subject matter the hub may be either fixed or rotatable in relation to the shaft section.

According to another aspect of the presently disclosed subject matter, in the case where the hub is fixed to the shaft section, the operator can advance the strain relief section into the storage chamber while keeping the strain relief section in engagement with the spiral groove, by rotating the strain relief section relative to the hub while gripping the hub.

On the other hand, in the case where the hub is rotatable relative to the shaft section, the operator can advance the strain relief section into the storage chamber while keeping the strain relief section in engagement with the spiral groove, by rotating the hub while gripping the shaft section. This ensures that even where that part of the strain relief section which is exposed to the exterior of the storage chamber becomes small when advancing the strain relief section into the storage chamber, the strain relief section can be advanced into the storage chamber assuredly and easily.

According to another aspect of the presently disclosed subject matter the strain relief section may have: a first member disposed at a distal end of the hub; and a second member which is disposed to protrude along a distal direction of the first member and which can be varied in the amount of protrusion relative to the first member.

According to another aspect of the presently disclosed subject matter, the effective length of the shaft section can be enlarged by reducing the amount of protrusion of the second member relative to the first member.

According to another aspect of the presently disclosed subject matter that surface of the first member which faces the second member may be formed with a first engagement part, and that surface of the second member which faces the first member may be formed with a second engagement part capable of engagement with the first engagement part.

According to another aspect of the presently disclosed subject matter, it is possible, by engaging the first engagement part and the second engagement part with each other, to restrain to an appropriate extent the displacement of the second member relative to the first member in the axial direction of the shaft section. As a result, it is possible, for example, to maintain a condition wherein the effective length of the shaft section has been enlarged.

According to another aspect of the presently disclosed subject matter the first and second members may be each formed in a belt-like shape and spirally wound around the shaft section.

According to another aspect of the presently disclosed subject matter, the strain relief section can be bent more easily, as compared with a case wherein the first and second members are each formed in a hollow cylindrical shape, for example. This ensures that the anti-kinking property can be suitably exhibited at the proximal-side portion of the shaft section.

According to another aspect of the presently disclosed subject matter, the strain relief section may be composed in a hollow shape.

This configuration ensures that the part, constituting the hollow part, of the strain relief section can be bent suitably, so that the anti-kinking property at the proximal-side portion of the shaft section can be exhibited suitably.

According to another aspect of the presently disclosed subject matter the catheter may further include a locking mechanism for maintaining a contracted state of the strain relief section after the strain relief section is contracted.

This configuration ensures that the strain relief section in the contracted state can be inhibited by the locking mechanism from returning to the original state by a restoring force (spring action) thereof. As a result, the strain relief section can be maintained in the contracted state, without needing the operator to hold down the strain relief section, for example.

The above-mentioned embodiments of a catheter may have a configuration wherein one side surface of the strain relief section is formed with a projection projecting to the hub side, whereas the other side surface of the strain relief section is formed with a recess corresponding to the projection. In this configuration, further, a contracted state of the strain relief section is maintained by engagement between the projection and the recess of adjacent spiral turns of the belt in the condition where the strain relief section has been contracted.

This configuration ensures that when the strain relief section is contracted, the projection and the recess of the adjacent spiral turns of the belt are engaged with each other. Therefore, an operation of contracting the strain relief section and an operation of locking the contracted state can be carried out with a single touch.

The above-mentioned embodiments of a catheter may have a configuration wherein the outer circumferential surface of the shaft section is formed with a projection which is located on the hub side relative to the distal end of the strain relief section in the condition where the strain relief section has been stretched and which projects outward in the radial direction of the shaft section. In this configuration, besides, the distal end of the strain relief section comes over the projection when the strain relief section is contracted, whereby the contracted state of the strain relief section is maintained.

This configuration ensures that when the strain relief section is contracted, the distal end of the strain relief section comes over the projection. Therefore, the operation of contracting the strain relief section and the operation of locking the contracted state can be performed with a single touch.

In the above-mentioned embodiments of a catheter, the locking mechanism may have a lock member which is disposed at the hub in the state of being movable to the proximal side of the hub and being capable of inhibiting distal movement of the shaft section, and the lock member may be capable of engagement with the strain relief section.

This configuration ensures that by moving the lock member to the proximal side of the hub in the state of being engaged with the strain relief section, it is possible to contract the strain relief section and to inhibit the strain relief section in the contracted state from returning to the original state by a restoring force thereof. In addition, it is possible, by regulating the amount of movement of the lock member, to lock the strain relief section in an arbitrary contracted state (amount of contraction).

According to another aspect of the presently disclosed subject matter, the strain relief section may have a configuration wherein the spiral turns other than the spiral turn on the most proximal side can be stored in the spiral turn on the most proximal side when the strain relief section is in a contracted state.

This configuration ensures that the strain relief section is compact when contracted, so that the amount of stretching of the effective length of the shaft section can be enlarged.

In the catheter as set forth above, that part of the outer circumferential surface of the shaft section which can be surrounded by the strain relief section may be presented with graduations by which the amount of enlargement of the effective length of the shaft section can be visually checked.

According to this configuration, the amount of enlargement of the effective length of the shaft section can be easily grasped and understood.

The catheter may have a configuration wherein the storage chamber is opening in a distal end surface of the hub, and a wall portion forming the opening of the storage chamber constitutes a stopper portion for locking the strain relief section stored in the storage chamber.

According to this configuration, the strain relief section stored in the storage chamber can be locked by the stopper portion. Therefore, the strain relief section can be suitably inhibited from coming out to the exterior through the opening of the storage chamber.

The above-mentioned embodiments of a catheter may have a configuration wherein the hub is flexible, and in which the wall portion of the hub which constitutes the storage chamber is formed with slits communicating with the opening.

This configuration ensures that by pushing the hub in a direction for enlarging the width of the slits to elastically deform the hub, it is possible to enlarge the area of the opening of the storage chamber. As a result, the strain relief section and the stopper portion can be restrained from interfering with each other when the strain relief section is stored into the storage chamber.

In the above-mentioned embodiments of a catheter, an outer surface of a distal portion of the stopper portion may be formed with a tapered surface which decreases in width toward the shaft section.

According to this configuration, the strain relief section can be guided into the storage chamber while sliding on the tapered surface of the stopper portion.

The catheter may include a disengagement-inhibiting mechanism for inhibiting a rear end portion of the strain relief section from being disengaged from the storage chamber.

According to this configuration, the disengagement-inhibiting mechanism is provided, whereby it is possible to inhibit the strain relief section from coming out of the storage chamber with the result of separation between the strain relief section and the hub.

In embodiments of the catheter, the first and second members may each be tapered along the distal direction of the shaft section.

According to this configuration, the flexibility of the shaft section can be enhanced along a direction from the proximal portion toward the distal end of the shaft section. This ensures that the anti-kinking property can be suitably exhibited at the proximal-side portion of the shaft section.

The catheter may have a configuration wherein either one of the first and second engagement parts is a projection, whereas the other of the first and second engagement parts is a projection or a recess.

According to this configuration, in the case where both of the first and second engagement parts are projections, it is possible by putting these projections into contact (engagement) with each other to suppress to an appropriate extent the displacement of the second member relative to the first member. In the case where one of the first and second engagement parts is a projection and the other is a recess, it is possible by bringing the projection into contact (engagement) with the recess to restrain to an appropriate extent the displacement of the second member relative to the first member.

In embodiments of the catheter, the first and second engagement parts may be screws capable of screw engagement with each other.

According to this configuration, it is possible, for example, to displace the second member toward the hub side by relatively rotating the first and second members. As a result, the amount of protrusion of the second member relative to the first member can be reduced. In addition, by regulating the amount of relative rotation of the first and second members, it is possible to arbitrarily set the amount of protrusion of the second member relative to the first member.

In embodiments of the catheter, a winding direction of the spiral of the first member and a winding direction of the spiral of the second member may be the same or reversed.

According to this configuration, the strain relief section can be bent more easily, as compared with a case where the first and second members are each formed in a hollow cylindrical shape, for example. As a result, the anti-kinking property can be suitably exhibited at the proximal-side portion of the shaft section.

In embodiments of the catheter, an outer circumferential surface of the second member may be formed with a projection for a sliding operation of the second member.

This configuration enables the operator to easily slide the second member while hooking a finger on the projection.

The catheter may have a configuration wherein at least either one of the outer circumferential surface of the shaft section, an outer circumferential surface of the first member, and the outer circumferential surface of the second member is provided with indication means by which the amount of protrusion of the second member relative to the first member can be checked.

According to this configuration, it is easy to grasp or understand the amount of protrusion of the second member relative to the first member (the enlargement of the effective length of the shaft section).

As has been described above, according to the presently disclosed subject matter, the effective length of the shaft section can be enlarged by displacing the distal end of the strain relief section toward the side where the hub is located. Therefore, even in the case where the blood vessel from the insertion instrument to the desired position in the living organ is comparatively long or meandering, it is possible to enlarge the effective length of the shaft section and thereby to cause the distal end of the shaft section to reach the desired position in the living organ. In this case, incidentally, the strain relief section is not omitted and, therefore, the anti-kinking property can be exhibited at the proximal-side portion of the shaft section. In addition, since the overall length of the catheter is not enlarged, excellent operability of the catheter can be maintained.

BRIEF DESCRIPTION OF DRAWINGS

FIG. 4 provides partial enlarged sectional views of a guiding catheter according to a third embodiment of the presently disclosed subject matter, wherein

FIG. 5 provides partial enlarged lateral views of a guiding catheter according to a fourth embodiment of the presently disclosed subject matter, wherein

FIG. 6 provides partial enlarged sectional views of a guiding catheter according to a fifth embodiment of the presently disclosed subject matter, wherein FIG. 6A is a partial enlarged sectional view showing an initial state of the guiding catheter, and FIG. 6B is a partial enlarged sectional view showing a state in which a strain relief section is contracted;

FIG. 7 provides partial enlarged lateral views of a guiding catheter according to a sixth embodiment of the presently disclosed subject matter, wherein FIG. 7A is a partial enlarged lateral view showing an initial state of the guiding catheter, and FIG. 7B is a partial enlarged lateral view showing a state in which a strain relief section is contracted;

FIG. 9 provides partial enlarged lateral views of a guiding catheter according to a seventh embodiment of the presently disclosed subject matter, wherein FIG. 9A is a partial enlarged lateral view showing an initial state of the guiding catheter, and FIG. 9B is a partial enlarged lateral view showing a state in which a strain relief section is contracted;

FIG. 12 provides partial enlarged sectional views of a shaft section, a hub, and a strain relief section shown in FIG. 11, wherein

FIG. 16 provides partial enlarged sectional views of the guiding catheter according to the ninth embodiment of the presently disclosed subject matter, wherein FIG. 16A is a partial enlarged sectional view showing an initial state of the guiding catheter, and FIG. 16B is a partial enlarged sectional view showing a state in which the strain relief section is stored in a storage chamber;

FIG. 19 provides partial enlarged sectional views of a shaft section, a hub, and a strain relief section shown in FIG. 18, wherein

FIG. 22 provides partial enlarged sectional views of a guiding catheter according to a twelfth embodiment of the presently disclosed subject matter, wherein FIG. 22A is a partial enlarged sectional view showing an initial state of the guiding catheter, and FIG. 22B is a partial enlarged sectional view showing a state in which the amount of protrusion of a second member relative to a first member is reduced;

FIG. 23 provides partial enlarged lateral views of a guiding catheter according to a thirteenth embodiment of the presently disclosed subject matter, wherein FIG. 23A is a partial enlarged lateral view showing an initial state of the guiding catheter, and FIG. 23B is a partial enlarged lateral view showing a state in which the amount of protrusion of a second member relative to a first member is reduced;

FIG. 25 provides partial enlarged sectional views of a guiding catheter according to a fourteenth embodiment of the presently disclosed subject matter, wherein

FIG. 26 provides partial enlarged sectional views of a guiding catheter according to a fifteenth embodiment of the presently disclosed subject matter, wherein FIG. 26A is a partial enlarged sectional view showing an initial state of the guiding catheter, and FIG. 26B is a partial enlarged sectional view showing a state in which the amount of protrusion of a second member relative to a first member is reduced; and FIG. 27 provides partial enlarged sectional views of a guiding catheter according to a sixteenth embodiment of the presently disclosed subject matter, wherein FIG. 27A is a partial enlarged sectional view showing an initial state of the guiding catheter, and FIG. 27B is a partial enlarged sectional view showing a state in which the amount of protrusion of a second member relative to a first member is reduced.

DETAILED DESCRIPTION OF EXEMPLARY EMBODIMENTS

Now, exemplary embodiments of catheters made in accordance with principles of the presently disclosed subject matter will be described in detail below, by showing exemplary embodiments and referring to the accompanying drawings.

First, a guiding catheter 10A (hereafter referred to simply as "catheter 10A") according to a first embodiment will be described referring to FIGS. 1 to 2B.

The catheter 10A is for use in the so-called PTCA (percutaneous transluminal coronary angioplasty) wherein a long shaft section 12 is inserted into a meandering blood vessel (for example, aorta) through an insertion instrument or the like, its distal portion is brought to an entrance of a coronary artery or the like, after which, for example, a balloon catheter is inserted into the inside of the shaft section 12 and guided through the entrance of the coronary artery or the like to a stenosed part generated inside the coronary artery or the like, and the balloon is inflated in the stenosed part to dilate the stenosed part, thereby treating the stenosis.

The presently disclosed subject matter is applicable not only to the above-mentioned PTCA but also to, for example, a catheter for improvement or diagnosis of a lesion formed in a living organ such as other blood vessels, bile duct, trachea, esophagus, urethra, and other organs.

Figure 1:
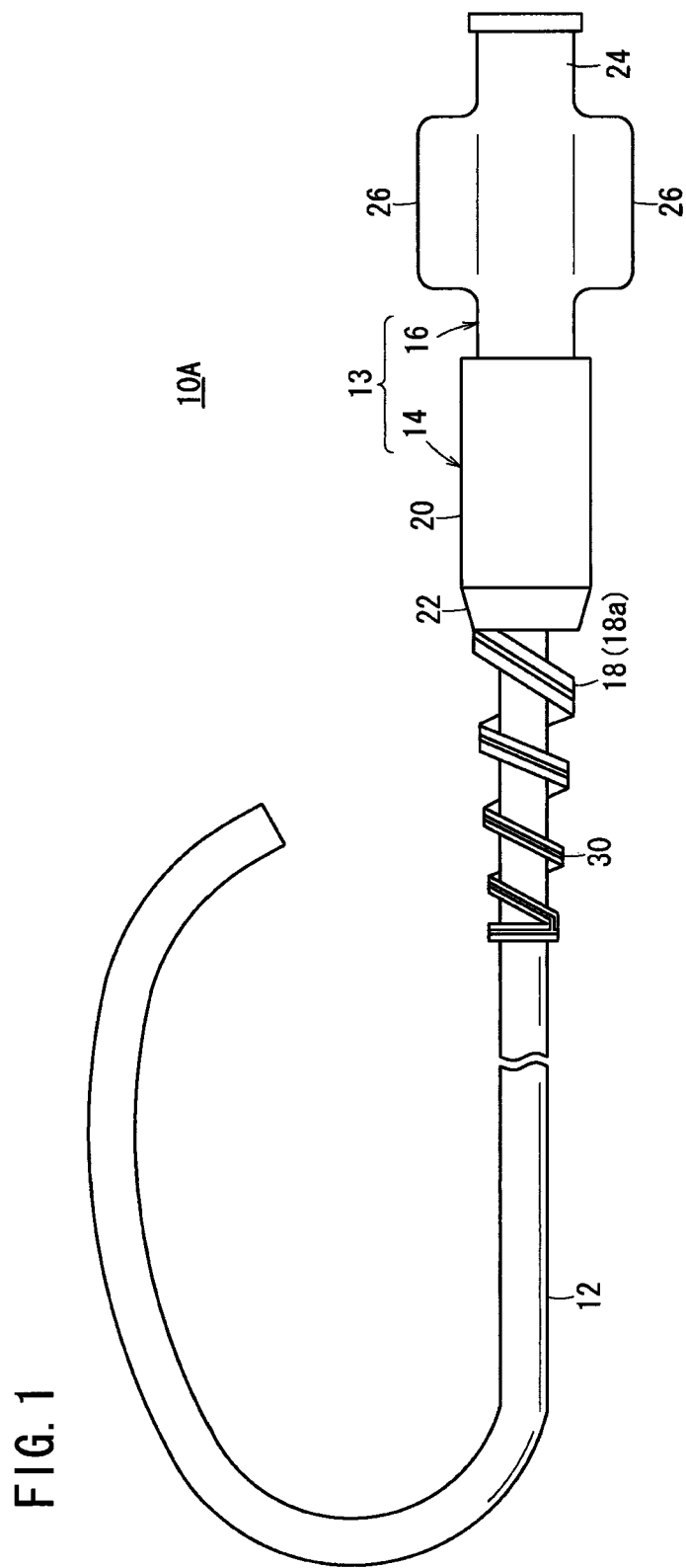
FIG. 1 is a general configuration view of a guiding catheter according to a first embodiment of the presently disclosed subject matter.

As shown in FIG. 1, the catheter 10A according to this embodiment includes a shaft section 12 which is small in diameter and long, a hub assembly 13, and a strain relief section (also called an anti-kinking protector, a crook-preventive section, a stress concentration avoiding section or a protective section) 18. The hub assembly 13 is connected to a proximal end of the shaft section 12, and the strain relief section 18 is disposed at a distal end of the hub assembly 13. It is to be noted here, however, that the shaft section 12 may extend to the inside (hollow part) of a hub 14 (described later) constituting the hub assembly 13.

The overall length of the catheter 10A (the distance from a distal end of the shaft section 12 to a rear end of the hub assembly 13) is set to be, for example, 100 cm, taking operability into consideration. Incidentally, the overall length of the catheter 10A may be set arbitrarily; for example, to be in the range of 90 to 110 cm.

The shaft section 12 is formed in a hollow cylindrical shape, and is formed from a highly slidable resin or the like. A guide wire (not shown), which is for guiding the catheter 10A to the entrance of the coronary artery or the like, a balloon catheter or the like is inserted into the inside of the shaft section 12. Incidentally, the shaft section 12 has an appropriate degree of flexibility and an appropriate degree of strength so that an operator can smoothly insert the shaft section 12 into a living organ such as a blood vessel while gripping and operating a proximal-side portion of the shaft section 12.

The length of the shaft section 12 is set on the basis of the length of the blood vessel from a position where the shaft section 12 is inserted into a living body to the entrance of the coronary artery or the like; for example, the length is set at 96 cm. Incidentally, the length of the shaft section 12 may be set arbitrarily (i.e., for a particular known surgical procedure or for a known anatomical architecture).

The hub assembly 13 has the hub 14 and a connector 16. The hub 14 is formed from a resin or the like, and can be higher in rigidity than the shaft section 12. The hub 14 is formed in a hollow shape, and can include a hub body 20 and a tapered section 22. The hub body 20 is formed in a hollow cylindrical shape, and is connected to the connector 16. Incidentally, an outer circumferential part in section of the hub body 20 is not limited to a circle but may be a polygon, oval, non-symmetrical shape, or the like. The tapered section 22 is disposed at a distal end of the hub body 20, and is decreased in diameter as one goes toward the shaft section 12.

The connector 16 can be formed from a resin or the like. The connector 16 includes an introduction section 24 formed in a hollow shape, and a pair of protruding sections 26, 26 which protrude outward from an outer circumferential surface of the introduction section 24. This enables a guide wire or the like to be inserted into and through the inside of the introduction section 24, the inside of the hub 24, and the inside of the shaft section 12.

Figure 2A:
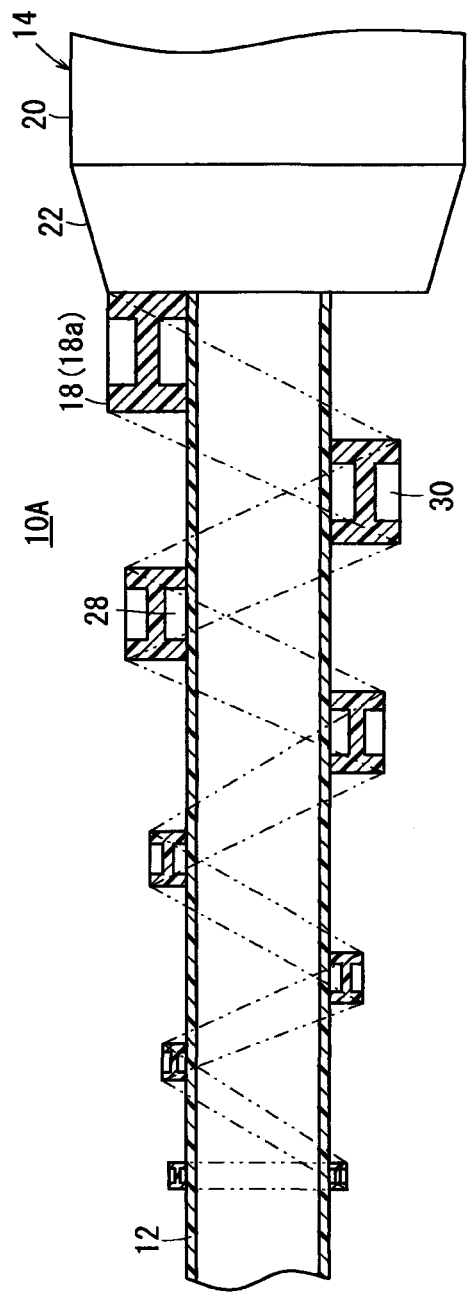
FIG. 2A is a partial enlarged sectional view showing an initial state of the guiding catheter shown in FIG. 1.

As shown in FIG. 2A, the strain relief section 18 can be formed as a structure wherein a belt body 18a, which can be flexible and fixed to a distal end face of the tapered section 22, is spirally wound around the shaft section 12 a plurality of times (in this embodiment, four times). This structure ensures that the strain relief section 18 is lower in rigidity than the hub 14. Incidentally, the strain relief section 18 is formed, for example, from a resin, a metal or the like.

The interval (pitch) between adjacent spiral turns of the belt body 18a is substantially constant. It is to be noted, however, that the interval may vary. In addition, a range where the belt body 18a is wound around the shaft section 12, or a range where the shaft section 12 is surrounded by the strain relief section 18, can be set arbitrarily. For example, this range is set to be a range of 8 cm from the proximal end of the shaft section 12.

Figure 2B:
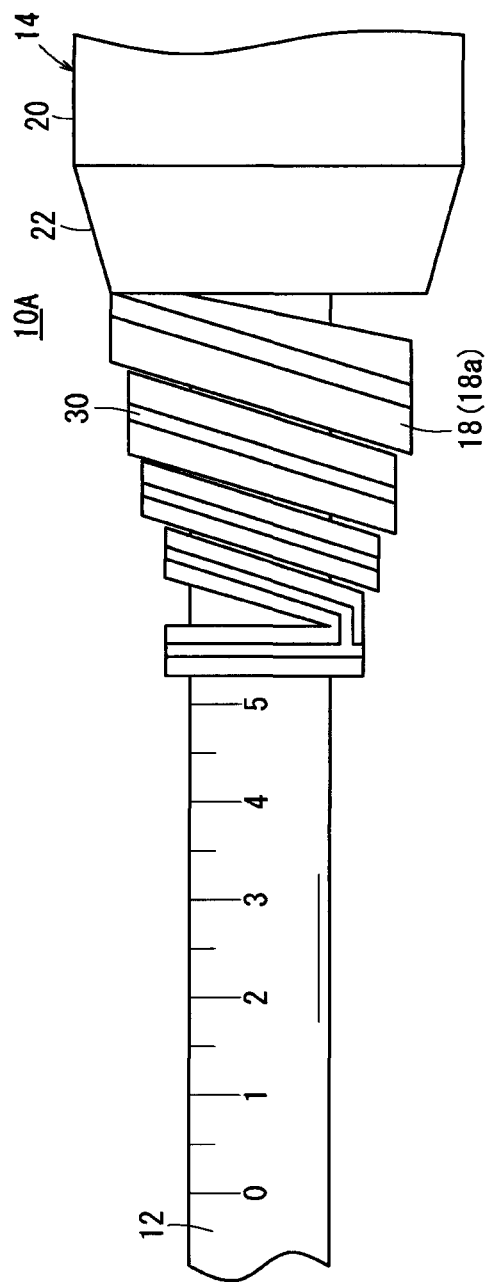
FIG. 2B is a partial enlarged lateral view showing a state in which a strain relief section is contracted.

Besides, as shown in FIG. 2B, predetermined numerals and graduations may be presented on that part of an outer circumferential surface of the shaft section 12 which is surrounded by the strain relief section 18. In the catheter 10A according to this embodiment, graduations are presented at an interval of 1 cm along an axial direction of the shaft section 12 (an axial direction of the hub 14), and numerals 0 to 8 are presented sequentially toward the hub 14 side, correspondingly to the graduations. In this case, as shown in FIG. 2B, an auxiliary graduation may be presented at a middle position between adjacent graduations. Incidentally, in FIG. 2B, numeral 6 and the latter numerals are hidden behind the strain relief section 18.

The strain relief section 18 (the belt body 18a) is gradually reduced in width and in thickness, along a distal direction of the shaft section 12.

An inner surface of the strain relief section 18 is in slidable contact with the outer circumferential surface of the shaft section 12. In addition, the inner surface of the strain relief section 18 is formed with an inside groove 28 which is roughly angular U-shaped in section. In other words, the inside groove 28 extends spirally. The groove width of the inside groove 28 is set at about half the width of the belt body 18a. Consequently, the inside groove 28 is gradually narrowed in width, along the distal direction of the shaft section 12. The groove depth of the inside groove 28 is set at about one third of the thickness of the belt body 18a. As a result, the inside groove 28 becomes gradually shallower, along the distal direction of the shaft section 12.

Frictional resistance between the inner surface of the strain relief section 18 and the outer circumferential surface of the shaft section 12 is roughly set at such a magnitude that the operator can slide the strain relief section 18 along the axial direction of the shaft section 12 by one hand. In other words, the strain relief section 18 is configured to be stretchable and contractible in the longitudinal axis (axial) direction of the shaft section 12.

An outer surface of the strain relief section 18 is formed with an outside groove 30 the shape of which is vertically inverse to that of the inside groove 28. In other words, the belt body 18a, formed with the inside groove 28 and the outside groove 30, is roughly H-shaped in section. Here, the shape of a distalmost end of the strain relief section 18 (the belt body 18a) is not particularly restricted; the distalmost end can be formed to be annular (closed ring) in shape. This ensures that, when the strain relief section 18 is slid relative to the outer circumferential surface of the shaft section 12, the strain relief section 18 can be suitably prevented from being disengaged from the shaft section 12.

In the catheter 10A configured as above, that part of the shaft section 12 which ranges from the distal end of the shaft section 12 to the distal end of the strain relief section 18 can be inserted into the living body (into the blood vessel) via a proximal portion of the insertion instrument. Incidentally, in the following description, the length from the distal end of the shaft section 12 to the distal end of the strain relief section 18 will be referred to as an effective length of the shaft section 12.

Now, operation of the catheter 10A according to this embodiment will be described below. First, for example, the form of the stenosed part in the living organ such as the coronary artery is determined by intravascular radiography or intravascular ultrasonic diagnosis, etc. Next, for example, by the Seldinger technique, a guide wire (not shown) is guided into the blood vessel percutaneously via a femoral region or the like, and the shaft section 12 of the catheter 10A is then inserted along the guide wire into the living organ.

In this instance, the shaft section 12 is inserted into the living organ while being curved, so that a stress is exerted on the proximal-side portion of the shaft section 12. When the stress is thus exerted, the proximal-side portion of the shaft section 12 is bent, and, along with this bending deformation, the strain relief section 18 is also deformed elastically. As a result, an anti-kinking property can be exhibited at the proximal-side portion of the shaft section 12. Accordingly, it is possible to suitably obviate a situation in which the stress would be concentrated on a joint part between the shaft section 12 and the tapered section 22 and the shaft section 12 might be bent sharply.

Then, under radioscopy, the guide wire (not shown) is advanced to the entrance of the coronary artery or the like, is let pass through the entrance and is placed inside the coronary artery or the like, and the shaft section 12 is advanced along the guide wire into the living organ. Subsequently, the distal end of the shaft section 12 arrives at the entrance of the coronary artery or the like, after which the guide wire is pulled out of the catheter 10A.

In this instance, in a case where the blood vessel from the position of insertion of the shaft section 12 into the living body to the entrance of the coronary artery or the like is comparatively long or where the blood vessel is meandering, the distal end of the strain relief section 18 may collide on the insertion instrument (or a skin) before the distal end of the shaft section 12 arrives at the entrance of the coronary artery or the like (i.e., target location). In other words, the effective length of the shaft section 12 may be insufficient and, accordingly, it may be difficult or impossible for the distal end of the shaft section 12 to reach the entrance of the coronary artery or the like (target location).

In such a case, first, the operator radioscopically or otherwise checks the insufficiency distance, namely, the distance from the distal end of the shaft section 12 to the entrance of the coronary artery or the like (target location). Then, when the insufficiency distance is about 3 cm, for example, the operator draws the distal end of the strain relief section 18 along a proximal direction of the shaft section 12 while sliding the strain relief section 18 relative to the outer circumferential surface of the shaft section 12. This results in that the interval between the adjacent spiral turns of the belt body 18a of the strain relief section 18 is reduced (or the adjacent spiral turns of the belt body 18a make contact with each other), whereby the strain relief section 18 is contracted in the axial direction of the shaft section 12.

Then, for example, the distal end of the strain relief section 18 is positioned in the vicinity of the graduation of 5 cm which is presented on the outer circumferential surface of the shaft section 12 (see FIG. 2B). This results in that the effective length of the shaft section 12 is enlarged by about 5 cm.

Thereafter, the shaft section 12 in this state is advanced further into the living organ by an amount corresponding to the insufficiency distance, whereby the distal end of the shaft section 12 is disposed at the entrance of the coronary artery or the like (target location).

Incidentally, in this instance, also, a stress may be exerted on the proximal-side portion of the shaft section 12. In this case, even if the adjacent spiral turns of the belt body 18a are for example in contact with each other, the strain relief section 18 can be easily deformed elastically along with the bending deformation of the shaft section 12, since the strain relief section 18 is formed with the inside groove 28 and the outside groove 30.

As a result, even with the strain relief section 18 in a contracted state, the anti-kinking property can be exhibited at the proximal-side portion of the shaft section 12, so that the shaft section 12 can be suitably restrained from being bent sharply.

Incidentally, advancing of the shaft section 12 further into the living organ in the condition wherein the effective length of the shaft section 12 has been enlarged may cause the distal end of the shaft section 12 to move past the entrance of the coronary artery or the like (target location). In such an instance, the strain relief section 18 may be a little stretched while pulling back the shaft section 12 toward the operator's side. As a result, a restoring force of the strain relief section 18 is weakened, so that the operator can maintain the contracted state of the strain relief section 18 without exerting a considerable force.

Thus, in the catheter 10A according to this embodiment, in the case where the effective length of the shaft section 12 is insufficient, the effective length of the shaft section 12 is enlarged by contracting the strain relief section 18 (displacing the distal end of the strain relief section 18 toward the side where the hub 14 is located). This makes it possible to cope with individual differences in shape, inclusive of the condition of meandering of the blood vessel into which the shaft section 12 is inserted, the length of the blood vessel, etc. In addition, it is unnecessary to utilize the guiding catheter 10A which has a large overall length, so that excellent operability can be maintained.

Besides, in this embodiment, the strain relief section 18 is formed to gradually decrease in width as one goes along the distal direction of the shaft section 12, so that the flexibility of the shaft section 12 can be enhanced along the direction from a proximal portion toward the distal end of the shaft section 12. As a result, the anti-kinking property can be suitably exhibited at the proximal-side portion of the shaft section 12.

In this embodiment, further, the inside groove 28 and the outside groove 30 are gradually decreased in width along the distal direction of the shaft section 12, and the inside groove 28 and the outside groove 30 are gradually decreased in depth along the distal direction of the shaft section 12. This ensures that, even where the adjacent spiral turns of the belt body 18a make contact with each other when the strain relief section 18 is contracted, the shaft section 12 can be gradually enhanced in flexibility along the distal direction of the shaft section 12. As a result, the anti-kinking property can be appropriately exhibited at the proximal-side portion of the shaft section 12 in the condition where the strain relief section 18 is contracted.

In this embodiment, the width and depth of the inside groove 28 and the outside groove 30 can be set arbitrarily. For instance, the width of the inside groove 28 and the outside groove 30 may be about one third of the width of the belt body 18a, or may be about three quarters of the width of the belt body 18a. The depth of the inside groove 28 and the outside groove 30 may be less than one third of the thickness of the belt body 18a.

In addition, the sectional shape of the inside groove 28 and the outside groove 30 is not restricted to the roughly angular U-shaped sectional shape, and can be an arbitrary shape. For example, a roughly semicircular sectional shape and a roughly V-shaped sectional shape can be adopted.

Further, in this embodiment, at least either one of the inside groove 28 or the outside groove 30 may be omitted.

Furthermore, the strain relief section 18 may not be in contact with the shaft section 12. In this case, if the outer circumferential surface of the shaft section 12 and the strain relief section 18 can make contact with each other when the proximal-side portion of the shaft section 12 is deformed, the anti-kinking property can be exhibited at the proximal-side portion of the shaft section 12.

The numerals presented on the outer circumferential surface of the shaft section 12 may be numerals corresponding to the distance from the distal end of the shaft section 12 to the distal end of the strain relief section 18. In this case, the effective length of the shaft section 12 that has been enlarged can be easily grasped or understood.

Now, a guiding catheter 10B (hereinafter referred to also as "catheter 10B") according to a second embodiment of the presently disclosed subject matter will be described below, referring to FIG. 3. Incidentally, with regard to the catheter 10B in the second embodiment, the same configurations as those of the catheter 10A in the first embodiment above are denoted by the same reference symbols as used above, and detailed description of the same reference structures will be omitted. This applies also to the third to eighth embodiments which will be described later.

Figure 3:
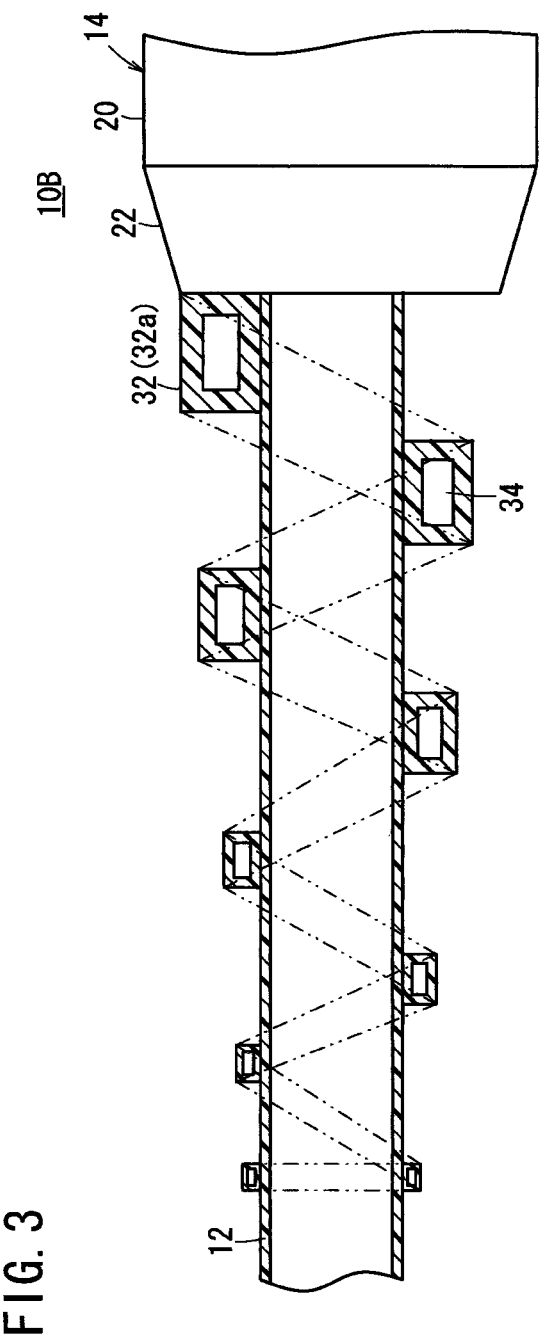
FIG. 3 is a partial enlarged sectional view of a shaft section, a hub, and a strain relief section of a guiding catheter according to a second embodiment of the presently disclosed subject matter.

As shown in FIG. 3, catheter 10B differs from the catheter 10A of the first embodiment with respect to the configuration of the strain relief section 32. Specifically, the strain relief section 32 is formed to be hollow in catheter 10B. More specifically, the strain relief section 32 is formed therein with a hole 34 which is substantially rectangular in sectional shape. Incidentally, the inside groove 28 and the outside groove 30 provided in the first embodiment are omitted in this second embodiment, and also in the third to eighth embodiments.

According to the catheter 10B in this embodiment, the strain relief section 32 is formed to be hollow, so that the strain relief section 32 can be easily deformed elastically, even in a case where adjacent spiral turns of a belt body 32a make contact with each other when the strain relief section 32 is contracted. Therefore, the anti-kinking property can be suitably exhibited at the proximal-side portion of the shaft section 12.

In this embodiment, the sectional shape of the hole 34 in the strain relief section 32 is not restricted to the substantially rectangular sectional shape, and may be an arbitrary shape. The sectional shape of the hole 34 may be a substantially circular sectional shape, for example.

Now, a guiding catheter 10C (hereinafter referred to also as "catheter 10C") according to a third embodiment of the presently disclosed subject matter will be described below, referring to FIGS. 4A and 4B.

Figure 4A:
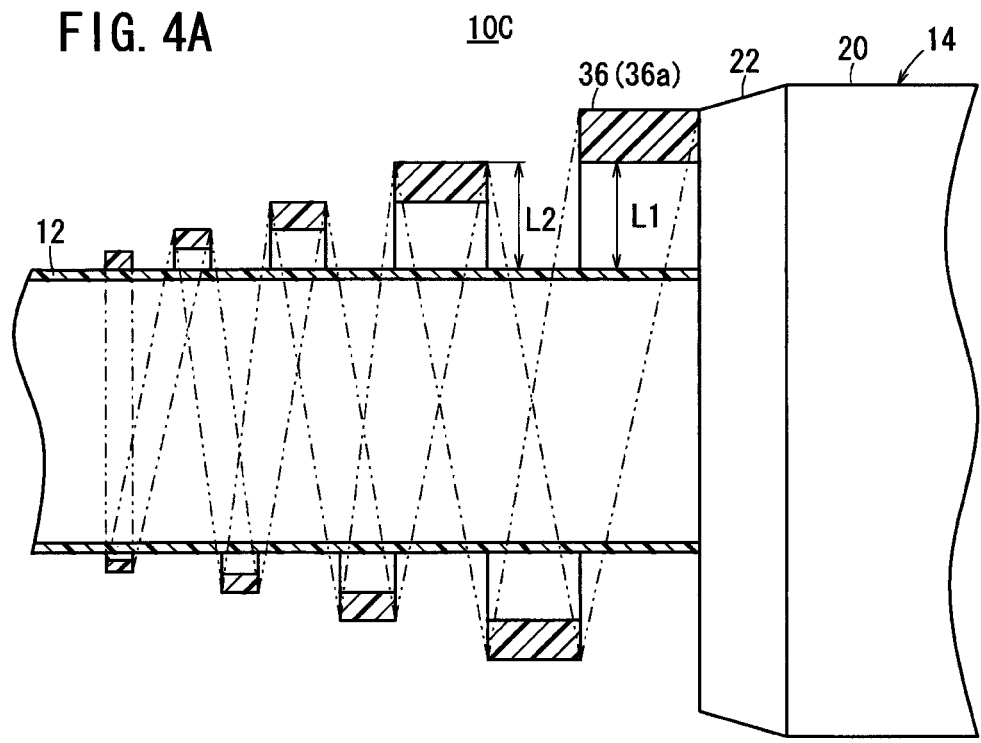
FIG. 4A is a partial enlarged sectional view showing an initial state of the guiding catheter.

As shown in FIG. 4A, this catheter 10C differs from the catheter 10A of the first embodiment with respect to the configuration of strain relief section 36. Specifically, the strain relief section 36 has a distal portion in contact with the outer circumferential surface of the shaft section 12, whereas portions other than the distal portion of the strain relief section 36 are not in contact with the outer circumferential surface of the shaft section 12. In addition, paying attention to a pair of adjacent spiral turns of a belt body 36a, a spacing L1 between the shaft section 12 and an inner surface of the spiral turn (of the belt body 36a) located on the side of the proximal end of the shaft section 12 is set to be wider than a spacing L2 between the shaft section 12 and an outer surface of the spiral turn (of the belt body 36a) located on the side of the distal end of the shaft section 12.

Figure 4B:
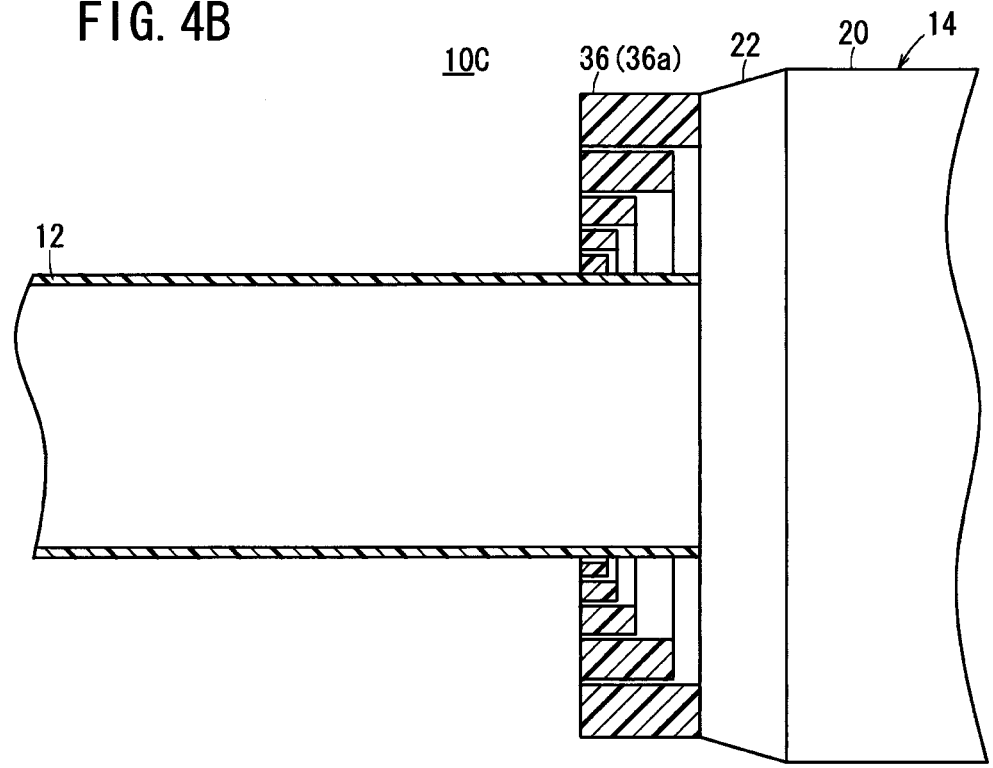
FIG. 4B is a partial enlarged sectional view showing a state in which a strain relief section is contracted.

According to the catheter 10C in this embodiment, in a condition where the strain relief section 36 is contracted, as shown in FIG. 4B, the spiral turns other than the spiral turn located on the most proximal side can all be stored inside the spiral turn on the most proximal side; therefore, the strain relief section 36 in this state is compact. As a result, the amount of extension of the effective length of the shaft section 12 can be enlarged.

Now, a guiding catheter 10D (hereinafter referred to also as "catheter 10D") according to a fourth embodiment of the presently disclosed subject matter will be described below, referring to FIGS. 5A and 5B. Incidentally, while the numerals and graduations presented on the shaft section 12 as above-mentioned (see FIG. 2B) are omitted from drawing in FIGS. 5A and 5B, the numerals and graduations can, in practice, be presented on the shaft section 12. This applies also to the other disclosed embodiments, including those in FIGS. 7A to 10.

Figure 5A:
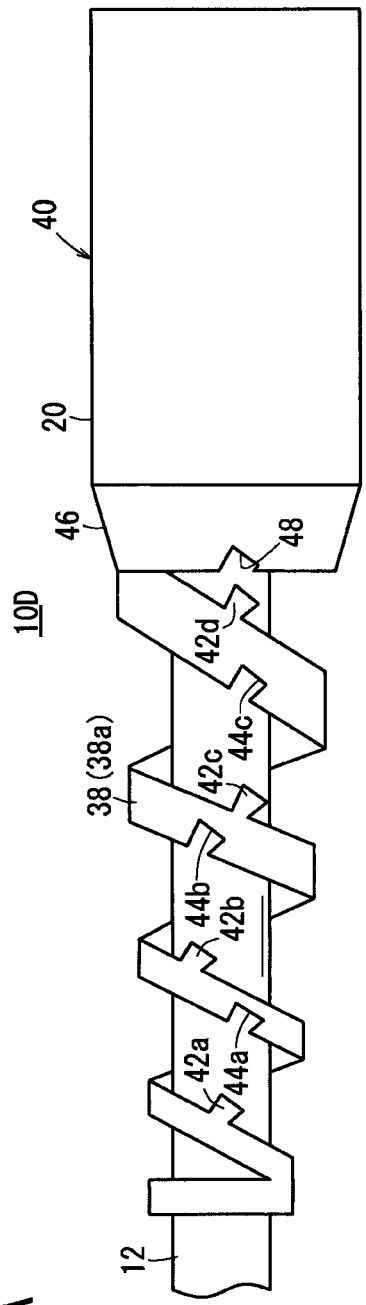
FIG. 5A is a partial enlarged lateral view showing an initial state of the guiding catheter.

As shown in FIG. 5A, catheter 10D differs from the catheter 10A of the first embodiment with respect to the configurations of a strain relief section 38 and a hub 40. Specifically, a side surface on one side (the side of the proximal end of the shaft section 12) of the strain relief section 38 is formed with plural (in FIG. 5A, four) projections 42a to 42d which are projected towards the hub 40 side (in the axial direction of the shaft section 12). These projections 42a to 42d are arranged with mutual offsets along a circumferential direction of the shaft section 12. Each of the projections 42a to 42d is formed in a roughly tetragonal shape in lateral view, while being gradually enlarged in width along the direction of projection.

In addition, a side surface on the other side (the side of the distal end of the shaft section 12) of the strain relief section 38 is formed with plural (in FIG. 5A, three) recesses 44a to 44c which correspond respectively to the projections 42a to 42c. These recesses 44a to 42c are arranged with some offset, along the circumferential direction of the shaft section 12, from positions for facing the projections 42a to 42c, respectively.

The hub 40 has the hub body 20 and a tapered section 46. The tapered section 46 is formed at its distal end with a recess 48 substantially the same in shape as the recesses 44a to 44c. The recess 48 faces the projection 42d.

Figure 5B:
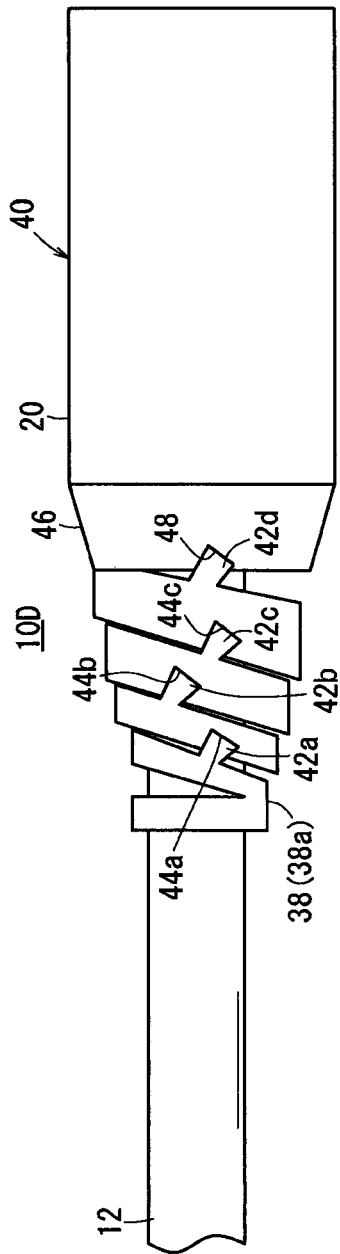
FIG. 5B is a partial enlarged lateral view showing a state in which a strain relief section is contracted.

According to the catheter 10D in this embodiment, when the strain relief section 38 is drawn along the proximal direction of the shaft section 12, as shown in FIG. 5B, the projection 42d located on the most hub 40 side fits into the recess 48 while deforming elastically, and the other projections 42a to 42c fit into the recesses 44a to 44c while deforming elastically.

As a result, predetermined frictional forces are generated between the projections 42a to 42c and the recesses 44a to 44c, and between the projection 42d and the recess 48. Consequently, the strain relief section 38 can be locked in a contracted state. Thus, in this embodiment, an operation of contracting the strain relief section 38 and an operation of locking the contracted state can be performed with a single touch.

In this embodiment, the numbers and the shapes of the projections 42a to 42d and the recesses 44a to 44c and 48 may be set arbitrarily. In short, it is only required that predetermined frictional forces should be generated when the projections 42a to 42d are engaged with the recesses 44a to 44c and 48.

Now, a guiding catheter 10E (hereinafter referred to as "catheter 10E") according to a fifth embodiment of the presently disclosed subject matter will be described below, referring to FIGS. 6A and 6B.

As shown in FIG. 6A, this catheter 10E differs from the catheter 10A of the first embodiment with respect to the configuration of strain relief section 50. Specifically, the strain relief section 50 includes a first part 52 located on the most proximal side with respect to the shaft section 12 and formed in a roughly trapezoidal sectional shape, an intermediate part 54 provided in succession to the first part 52, and a second part 56 located on the most distal side with respect to the shaft section 12 and provided in succession to the intermediate part 54.

The first part 52 is spirally wound around the shaft section 12 only one time. Of the first part 52, a side surface on the side of the distal end of the shaft section 12 is formed in a tapered shape, with its diameter gradually decreased along the distal direction. In addition, this side surface is formed with a first cutout 58 in its part adjacent to the shaft section 12.

The intermediate part 54 is spirally wound around the shaft section 12 twice. The intermediate part 54 can include: a first inside part 60 formed in a roughly parallelogrammatic sectional shape in contact with the outer circumferential surface of the shaft section 12; and a first outside part 62 disposed at a portion of an outer surface of the first inside part 60 and formed in a roughly parallelogrammatic sectional shape. The first outside part 62 protrudes along the distal direction of the shaft section 12, relative to the first inside part 60.

This results in that the first inside part 60 has a portion protruding toward the hub 14 side, relative to the first outside part 62. In addition, the shape of an end part of this protruding portion (protrusion) 60a (an end part on one side of the first inside part 60) corresponds to the shape of the first cutout 58. Incidentally, the amount of protrusion of the protruding portion 60a is set to be greater than the length of the first cutout 58 along the axial direction of the shaft section 12.

In addition, the intermediate part 54 is formed with a second cutout (recess) 64, defined by both that portion of the first outside part 62 which protrudes along the distal direction of the shaft section 12 relative to the first inside part 60 and an end portion on the other side of the first inside part 60. Incidentally, the second cutout 64 can be substantially the same shape as the first cutout 58.

The second part 56 is spirally wound around the shaft section 12 only one time. The second part 56 can include: a second inside part 66 formed in a roughly trapezoidal sectional shape in contact with the outer circumferential surface of the shaft section 12; and a second outside part 68 disposed at a portion of an outer surface of the second inside part 66 and formed in a roughly square sectional shape. The second outside part 68 can be located at a distal end of the strain relief section 50.

According to the catheter 10E in this embodiment, when the strain relief section 50 is drawn along the proximal direction of the shaft section 12, as shown in FIG. 6B, a portion of the protruding portion 60a of the intermediate part 54 fits into the first cutout 58 while deforming elastically, and the other portion of the protruding portion 60a fits into a portion of the second cutout 64 while deforming elastically. Further, an end portion on the hub 14 side of the second inside part 66 fits into the other portion of the second cutout 64 while deforming elastically. This ensures that predetermined frictional forces are generated respectively between the protruding portion 60a and the first cutout 58, between the protruding portion 60a and the second cutout 64, and between the second inside part 66 and the second cutout 64. Consequently, the strain relief section 50 is locked in a contracted state.

In addition, a first gap 70 is formed between the first part 52 and the first outside part 62, a second gap 72 and a third gap 74 are each formed between adjacent spiral turns of the first outside part 62, and a fourth gap 76 is formed between the first outside part 62 and the second outside part 68. Therefore, in the condition where the strain relief section 50 is contracted, the strain relief section 50 can be easily deformed elastically along with the bending deformation of the shaft section 12. Accordingly, the anti-kinking property can be effectively exhibited at the proximal-side portion of the shaft section 12.

In this embodiment, the shapes of the protruding portion 60a, the first cutout 58, the second cutout 64, and the second inside part 66 may be set arbitrarily. For example, a configuration may be adopted wherein the protruding portion 60a is gradually increased in width along the direction toward the hub 14 side, the shape of an end portion on the hub 14 side of the second inside part 66 is the same as the shape of the protruding portion 60a, and the shapes of the first and second cutouts 58 and 64 correspond to the shape of an end portion of the protruding portion 60a. In this case, the contracted state of the strain relief section 50, once locked, is prevented from being easily unlocked.

Now, a guiding catheter 10F (hereinafter referred to also as "catheter 10F") according to a sixth embodiment of the presently disclosed subject matter will be described below, referring to FIGS. 7A to 8.

As shown in FIG. 7A, this catheter 10F differs from the catheter 10A of the first embodiment with respect to the configurations of shaft section 78 and strain relief section 80. Specifically, the shaft section 78 is formed at an outer circumferential surface thereof with a projection 82 which is located on the hub 14 side relative to a distal end of the strain relief section 80 in an initial state of the guiding catheter 10F (a state wherein the strain relief section 80 is stretched) and which projects outward in a radial direction of the shaft section 78. The projection 82 is formed in an annular shape at the outer circumferential surface of the shaft section 78.

In addition, the projection 82 is located a little on the proximal side of the middle of that part of the shaft section 78 which is surrounded by the strain relief section 80. It is to be noted here, however, that the projection 82 may be disposed at an arbitrary position of that part of the shaft section 78 which is surrounded by the strain relief section 80.

The height (amount of projection) of the projection 82 is set at such a level that the strain relief section 80 in a bent state can be made to come over the projection 82.

According to the catheter 10F in this embodiment, when the strain relief section 80 is drawn along the proximal direction the shaft section 78, as shown in FIG. 7B, the distal end of the strain relief section 80 comes over the projection 82. Therefore, the strain relief section 80 can be locked in its contracted state. This ensures that an operation of contracting the strain relief section 80 and an operation of locking the contracted state can be performed with a single touch.

In this embodiment, the projection 82 is formed in the annular shape at the outer circumferential surface of the shaft section 78. This ensures that the strain relief section 80 having once ridden over the projection 82 can be suitably restrained from riding again over the projection 82 by its restoring force (spring action).

Figure 8:
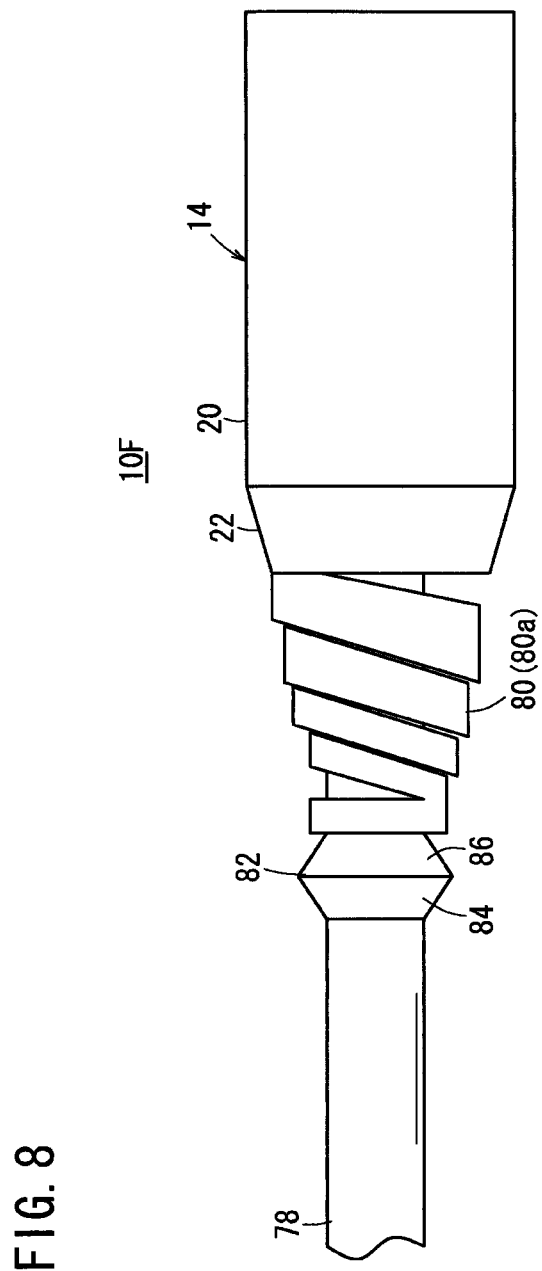
FIG. 8 is a partial enlarged lateral view showing a modification of the guiding catheter according to the sixth embodiment of the presently disclosed subject matter.

In this embodiment, the projection 82 may includes a first tapered section 84 increasing in diameter toward the proximal side in an axial direction of the shaft section 78, and a second tapered section 86 being continuous with the first tapered section 84 and decreasing in diameter toward the proximal side in the axial direction of the shaft section 78, as shown in FIG. 8.

In this case, at the time of drawing the strain relief section 80 toward the hub 14 side, the strain relief section 80 can be made to smoothly slide on the first tapered section 84. In addition, the provision of the second tapered section 86 ensures that, at the time of stretching the strain relief section 80 in the contracted state, the strain relief section 80 can be made to smoothly slide on the second tapered section 86. Incidentally, in this modification, the second tapered section 86 may be omitted.

Besides, in this embodiment, the configuration of the projection 82 is not restricted to the annular shape, and the projection 82 may be formed in an arbitrary shape. For example, the projection 82 may be formed in an arcuate shape or a rectangular shape at the outer circumferential surface of the shaft section 78.

Furthermore, the catheter 10F in this embodiment may be provided with a plurality of projections 82 at the outer circumferential surface of the shaft section 78.

Figure 10:
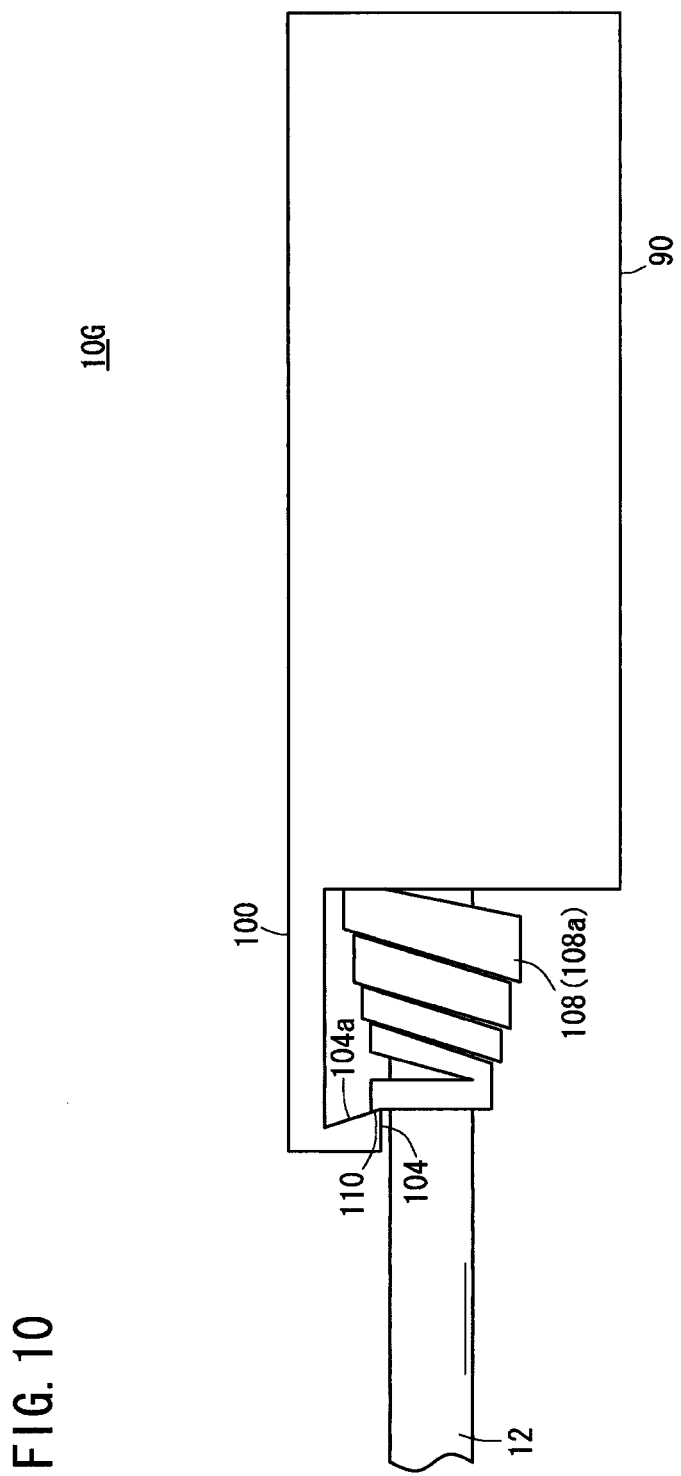
FIG. 10 is a partial enlarged lateral view showing a modification of the guiding catheter according to the seventh embodiment of the presently disclosed subject matter.

Now, a guiding catheter 10G (hereinafter referred to also as "catheter 10G") according to a seventh embodiment of the presently disclosed subject matter will be described below, referring to FIGS. 9A to 10.

As shown in FIG. 9A, this catheter 10G differs from the catheter 10A of the first embodiment with respect to configurations of hub 88 and strain relief section 108. Specifically, the hub 88 includes a hub body 90 formed to be a size slightly greater than the hub body 20 in the first embodiment, and a locking mechanism 92 disposed at the hub body 90. Incidentally, in this embodiment, the tapered section 22 in the first embodiment is omitted.

A distal end face of the hub body 90 is formed with a hole 94 extending in the axial direction of the shaft section 12, and an outer circumferential surface of the hub body 90 is formed with a slot 96 communicating with the hole 94. The depth of the hole 94 is set to be slightly smaller than the length of a lock member 100 which will be described later. Incidentally, the hole 94 may pierce through the hub body 90.

In addition, a wall surface of the hole 94 is provided with a plurality of first engagement teeth 98 in succession along a depth direction of the hole 94. The range in which the first engagement teeth 98 are formed may be determined arbitrarily. Each of the first engagement teeth 98 is formed to be roughly triangle-shaped in section, wherein a tooth surface 98a located on the distal side forms a long side of the triangle, and a tooth surface 98b located on the side of the connector 16 forms a short side of the triangle.

The locking mechanism 92 includes the flexible lock member 100 extending in one direction and disposed near and in the hole 94 of the hub body 90, and an unlocking lever 102 provided in the vicinity of a one-side end portion of the lock member 100.

The lock member 100 can include a portion inserted in the hole 94 and an other portion located outside the hole 94. In addition, the lock member 100 can be formed, at its end portion on the other side (the side located outside of the hole 94), with a contact part 104 projecting toward the shaft section 12. That surface of the contact part 104 which faces the hub body 90 is formed in a tapered shape gradually increased in width along a projecting direction of the contact part 104.

The outside diameter of the lock member 100 is set to be a little smaller than the bore diameter of the hole 94. The lock member 100 can be formed, at its portion ranging from its other end to a position slightly on the distal side of its middle, with a plurality of second engagement teeth 106 capable of engagement with the first engagement teeth 98. This ensures that the second engagement teeth 106 can always be engaged with the first engagement teeth 98, irrespectively of the position of the lock member 100.

Each of the second engagement teeth 106 is roughly triangle-shaped in section, wherein a tooth surface 106a located on the distal side forms a short side of the triangle, and a tooth surface 106b located on the connector 16 side forms a long side of the triangle.

As a result, the lock member 100 is so configured that, in the condition where the first and second engagement teeth 98 and 106 are engaged (meshed) with each other, a force needed to move the lock member 100 along the distal direction of the shaft section 12 is greater than a force needed to move the lock member 100 toward the connector 16 side. In other words, the lock member 100 is difficult to move along the distal direction of the shaft section 12 but is easy to move toward the connector 16 side (the proximal side).

Incidentally, the number of teeth of the first engagement teeth 98 and the shapes of the first and second engagement teeth 98 and 106 are so set that the lock member 100 is not moved along the distal direction of the shaft section 12 when a restoring force upon contraction of the strain relief section 108 acts on the lock member 100.

Incidentally, in this embodiment, the strain relief section 108 is formed, at a distal portion thereof, with a tapered surface 110 corresponding to a tapered surface 104a of the contact part 104. In addition, the unlocking lever 102 is exposed to the exterior of the hub body 90 through the slot 96.

According to the guiding catheter 10G in this embodiment, when the lock member 100 is drawn toward the connector 16 side, the second engagement teeth 106 come over the first engagement teeth 98. This results in that the lock member 100 is moved toward the connector 16 side, and the tapered surface 104a of the contact part 104 makes contact with the tapered surface 110 at a distal end of the strain relief section 108. When the lock member 100 is further drawn, the strain relief section 108 comes to be contracted, as shown in FIG. 9B. In this instance, since the first engagement teeth 98 and the second engagement teeth 106 are in an engaged state, the contracted state of the strain relief section 108 can be locked. Accordingly, an operation of contracting the strain relief section 108 and an operation of locking the contracted state can be performed with a single touch.

Incidentally, when it is desired to extend the strain relief section 108, the unlocking lever 102 is pulled upward. This disengages the first and second engagement teeth 98 and 106 from each other, resulting in that the lock member 100 can be easily moved along the distal direction of the shaft section 12.

According to the catheter 10G in this embodiment, the second engagement teeth 106 can always be in engagement with the first engagement teeth 98, irrespectively of the position of the lock member 100. Therefore, the strain relief section 108 can be locked in an arbitrary contracted state.

The catheter 10G according to this embodiment is not restricted to the above-described configuration. For example, the lock member 100 may be fixed to the distal end face of the hub body 90, as shown in FIG. 10. In this case, by drawing the strain relief section 108 toward the hub body 90 side and positioning the distal end of the strain relief section 108 to the hub body 90 side relative to the contact part 104, the contracted state of the strain relief section 108 can be locked suitably.

In this embodiment, the contact part 104 may be formed to be rectangular in shape in lateral view.

Now, a guiding catheter 10H (hereinafter referred to also as "catheter 10H") according to an eighth embodiment of the presently disclosed subject matter will be described below, referring to FIGS. 11 to 13.

Figure 11:
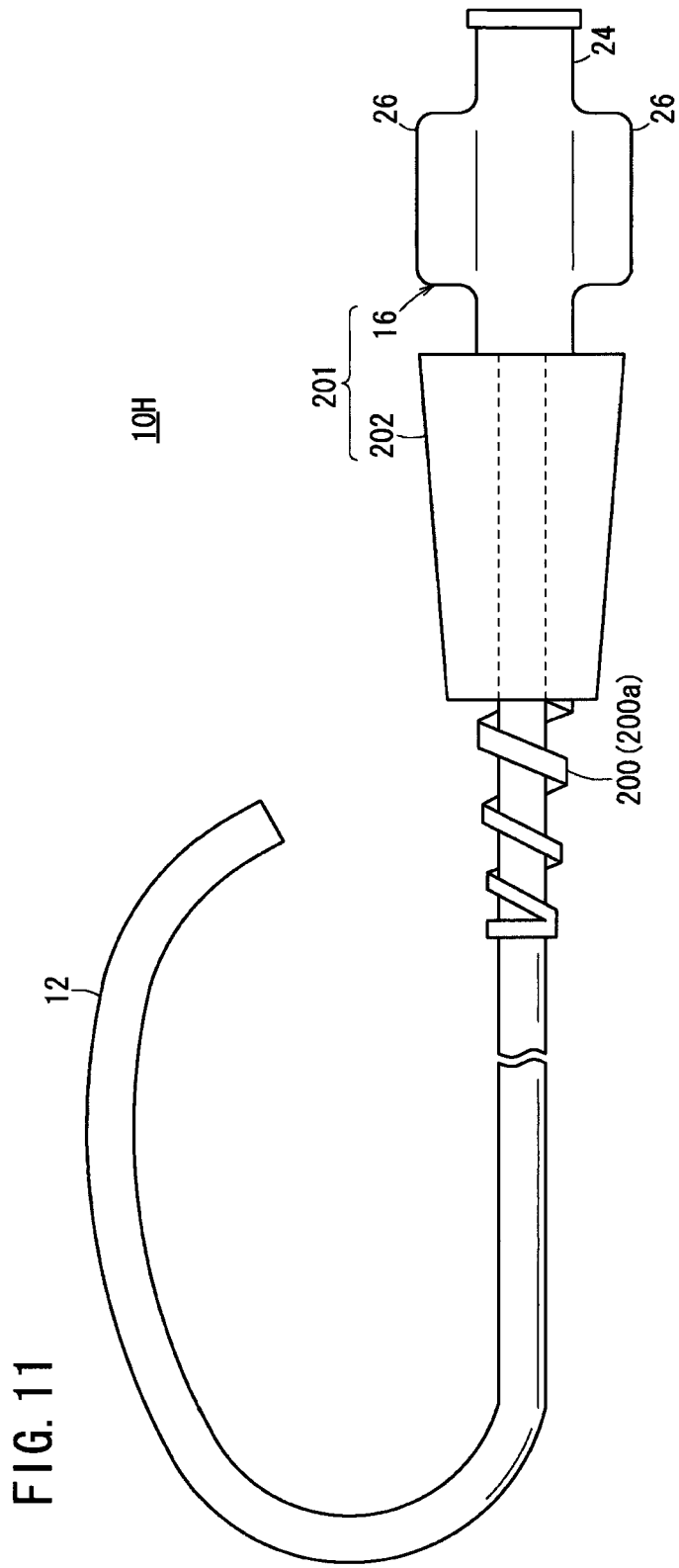
FIG. 11 is a general configuration view of a guiding catheter according to an eighth embodiment of the presently disclosed subject matter.
Figure 12A:
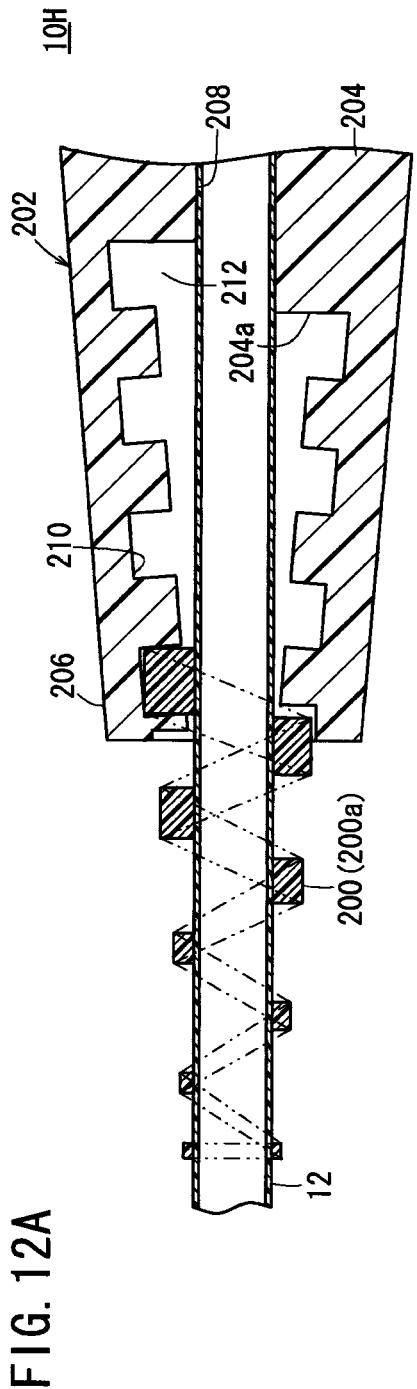
FIG. 12A is a partial enlarged sectional view showing an initial state of the guiding catheter.
Figure 12B:
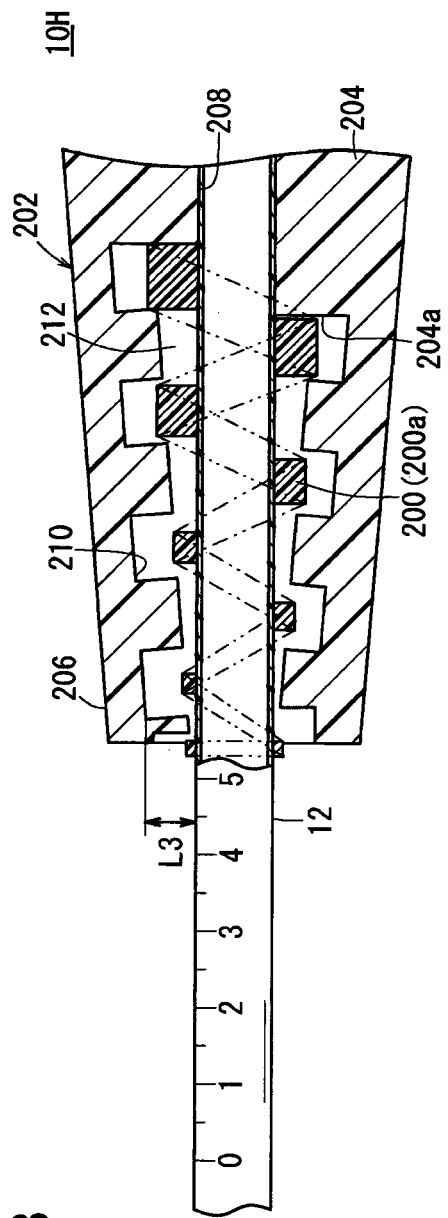
FIG. 12B is a partial enlarged sectional view showing a state in which the strain relief section is stored in a storage chamber.

As shown in FIGS. 11 to 12B, this catheter 10H differs from the catheter 10A of the first embodiment with respect to the configurations of strain relief section 200 and hub assembly 201. In this embodiment, the hub assembly 201 is so disposed as to surround the proximal portion of the shaft section 12 (see FIG. 12A), and includes a hub 202 and the connector 16. Incidentally, the distance from a distal end of the strain relief section 200 to a distal end of the hub 202 is set to be 5 cm, for example.

As shown in FIG. 12B, predetermined numerals and graduations are presented on that portion of the outer circumferential surface of the shaft section 12 which is located between the distal end of the strain relief section 200 and the distal end of the hub 202. In the catheter 10H according to this embodiment, the graduations are presented at an interval of 1 cm along the axial direction of the shaft section 12 (an axial direction of the hub 202). In addition, numerals 0 to 5 are presented correspondingly to the graduations, along a direction toward the hub 202 side. In FIG. 12B, an auxiliary graduation is presented at a middle position between adjacent graduations.

The hub 202 is formed in a tapered shape gradually decreased in diameter along the distal direction of the shaft section 12. In addition, the hub 202 includes a first part 204 connected to the connector 16, and a second part 206 which is located at a distal end of the first part 204 and which is provided with the strain relief section 200.

The first part 204 is formed therein with a through-hole 208 along the axial direction of the shaft section 12. The proximal portion of the shaft section 12 is fixed to the first part 204, in a state of being inserted in the through-hole 208.

The second part 206 is formed in a hollow cylindrical shape, and is projected from a distal end surface 204a of the first part 204 along the proximal direction of the shaft section 12. In other words, the second part 206 is surrounding a proximal-side portion of the shaft section 12.

An outer circumferential surface of the first part 204 and an outer circumferential surface of the second part 206 can be integral with each other, and form a continuous tapered surface which is decreased in diameter along the distal direction of the shaft section 12. In addition, an inner circumferential surface of the second part 206 is formed in a tapered shape which is decreased in diameter along the distal direction of the shaft section 12 in a state of being spaced from the shaft section 12. Incidentally, in the second part 206, the taper angle of the outer circumferential surface and the taper angle of the inner circumferential surface are set to be substantially equal.

The inner circumferential surface of the second part 206 can be formed with a spiral groove 210 along the axial direction of the shaft section 12. This results in that the spiral groove 210 spreads outward in a radial direction of the shaft section 12 as one goes toward the first part 204.

The spiral groove 210 is formed to be rectangular in sectional shape, and is extended around the shaft section 12 three times. The pitch of the spiral groove 210 corresponds to the pitch of the spiral of the above-mentioned strain relief section 200.

The width and the depth of the spiral groove 210 are set to be constant. Specifically, the width of the spiral groove 210 is a little greater than the width of a belt body 200a located on a proximal portion (rear end portion) of the strain relief section 200, and the depth of the spiral groove 210 is smaller than the thickness of the belt body 200a.

At an end portion (starting end portion), located on the distal side with respect to the shaft section 12, of the spiral groove 210, a spacing L3 between a groove bottom surface and the shaft section 12 is set to be slightly smaller than the thickness of a spiral turn, located at the proximal portion of the strain relief section 200, of the belt body 200a (see FIG. 12B, also). In an initial state of the catheter 10H, the proximal portion of the strain relief section 200 can be disposed in a bent state in the starting end portion of the spiral groove 210. This ensures that the strain relief section 200 can be prevented from coming out of the spiral groove 210 to cause separation of the strain relief section 200 and the hub 202 from each other. In other words, the starting end portion of the spiral groove 210 functions as a disengagement-inhibiting mechanism.

The inner circumferential surface of the second part 206 terminates at the distal end surface 204a of the first part 204. As a result, a storage chamber 212 is defined by the distal end surface 204a of the first part 204 and the inner circumferential surface of the second part 206. The storage chamber 212 communicates with the through-hole 208, and is opening to the distal side with respect to the shaft section 12.

According to the catheter 10H in this embodiment, as shown in FIG. 12B, when the strain relief section 200 is rotated clockwise as viewed from the proximal side with respect to the catheter 10H, the strain relief section 200 can be advanced into the storage chamber 212 while in engagement with the spiral groove 210. This makes it possible to displace the distal end of the strain relief section 200 toward the hub 202 side, and thereby to enlarge the effective length of the shaft section 12.

Even in a case where a stress is exerted on the proximal-side portion of the shaft section 12 in a condition where the effective length of the shaft section 12 is enlarged as above-mentioned, the strain relief section 200 stored in the storage chamber 212 can be elastically deformed along with a bending deformation of the shaft section 12. Consequently, the anti-kinking property can be suitably exhibited at the proximal-side portion of the shaft section 12.

Besides, in this embodiment, by rotating the strain relief section 200, the strain relief section 200 is advanced into the storage chamber 212 while in engagement with the spiral groove 210. Therefore, by regulating the amount of rotation of the strain relief section 200, it is possible to arbitrarily set the amount by which the effective length of the shaft section 12 is enlarged.

Furthermore, the number of turns of spiral (three) of the spiral groove 210 is set to be smaller than the number of turns of spiral (four) of the strain relief section 200. This ensures that, in a condition where the proximal portion of the strain relief section 200 is in contact with the distal end surface 204a of the first part 204, a distal portion of the strain relief section 200 can be disposed protruding from a distal end of the second part 206. As a result, the strain relief section 200 can be suitably prevented from being moved excessively deep into the storage chamber 212. Accordingly, the strain relief section 200 having been stored in the storage chamber 212 can be easily taken out to the exterior of the storage chamber 212.

In this embodiment, the strain relief section 200 is formed to gradually decrease in width along the distal direction of the shaft section 12. Therefore, the flexibility of the shaft section 12 can be enhanced along the direction from the proximal portion toward the distal end of the shaft section 12. This ensures that the anti-kinking property can be suitably exhibited at the proximal-side portion of the shaft section 12.

Figure 13:
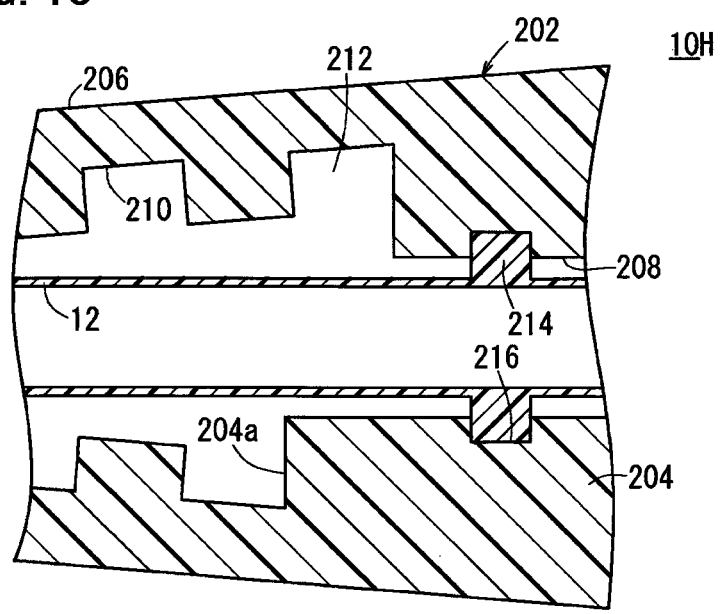
FIG. 13 is a partial enlarged sectional view showing a modification of the guiding catheter according to the eighth embodiment of the presently disclosed subject matter.

In this embodiment, as represented by the catheter 10H according to a modification shown in FIG. 13, the hub 202 may not necessarily be fixed to the shaft section 12. Specifically, the hub 202 may be provided to be rotatable relative to the shaft section 12. More specifically, a configuration may be adopted wherein the outer circumferential surface of the shaft section 12 is formed with an annular projection 214, and a wall surface of the through-hole 208 is formed with an annular recess 216 in which the annular projection 214 can be disposed. This ensures that the hub 202 is rotatable relative to the shaft section 12, in a state of being restrained from moving along the axial direction of the shaft section 12.

In this case, for example, by rotating the hub 202 clockwise as viewed from the proximal side with respect to the catheter 10H while gripping the strain relief section 200, the operator can advance the strain relief section 200 into the storage chamber 212 while keeping the strain relief section 200 in engagement with the spiral groove 210. As a result, the effective length of the shaft section 12 can be enlarged by operating the hub 202 while preventing rotation of the shaft section 12. This ensures that, even where that part of the strain relief section 200 which is exposed from the distal end of the second part 206 becomes small at the time of advancing the strain relief section 200 into the storage chamber 212, the strain relief section 200 can be advanced into the storage chamber 212 assuredly and easily.

In FIG. 13, the annular projection 214 is formed to be roughly square in sectional shape, and the annular recess 216 is formed to be rectangular in sectional shape. However, the sectional shapes of the annular projection 214 and the annular recess 216 can be set arbitrarily. In addition, the sizes of the annular projection 214 and the annular recess 216 can also be set arbitrarily.

In this embodiment, the pitch of spiral of the strain relief section 200 and the pitch of spiral of the spiral groove 210 can be set arbitrarily. Since the strain relief section 200 is flexible and is stretchable and contractible, the strain relief section 200 can be engaged with the spiral groove 210 even if there is some discrepancy between these pitches.

In this embodiment, the number of turns of spiral of the strain relief section 200 and the number of turns of spiral of the spiral groove 210 can be set arbitrarily. The shape of a distalmost end of the strain relief section 200 (the belt body 200a) is not particularly restricted; the shape can be an annular shape (closed ring). This ensures that, when the strain relief section 200 is stored into the storage chamber 212 or taken out of the storage chamber 212, the strain relief section 200 can be suitably prevented from being disengaged from the shaft section 12.

In this embodiment, the numerals presented on the outer circumferential surface of the shaft section 12 may be numerals which correspond to the distance from the distal end of the shaft section 12 to the distal end of the strain relief section 200. In this case, the effective length of the shaft section 12 that has been enlarged can be easily grasped or understood.

Now, a guiding catheter 10I (hereinafter referred to also as "catheter 10I") according to a ninth embodiment of the presently disclosed subject matter will be described below, referring to FIGS. 14 to 16B. Incidentally, the catheter 10I in this ninth embodiment can include the same configuration as the catheter 10H in the eighth embodiment and similar structures are denoted by the same reference symbols as used above, and detailed descriptions of them will be omitted.

Figure 14:
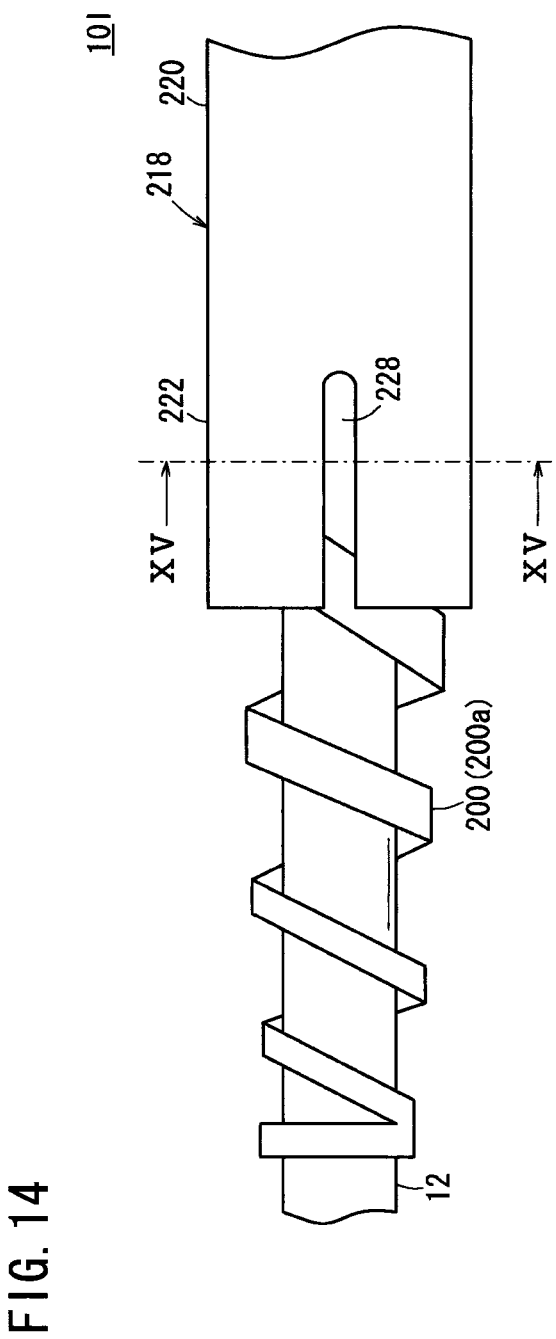
FIG. 14 is a partial enlarged lateral view of a shaft section, a hub, and a strain relief section of a guiding catheter according to a ninth embodiment of the presently disclosed subject matter.
Figure 15:
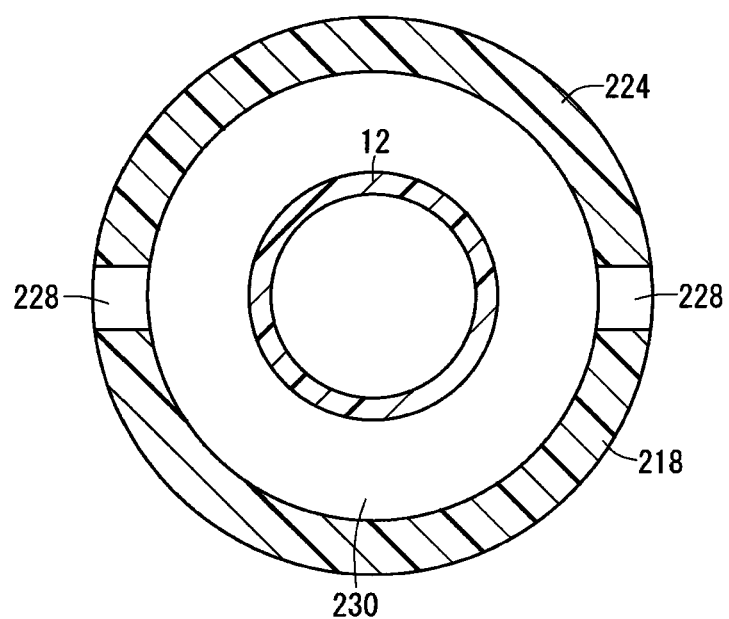
FIG. 15 is a sectional view taken along a line XV-XV of FIG. 14.

As shown in FIG. 14, this catheter 10I differs from the catheter 10H of the eighth embodiment with respect to the configuration of hub 218. Specifically, the hub 218 is formed in a hollow cylindrical shape, the diameter of which is substantially constant. Incidentally, an outer circumference in section of the hub 218 is not restricted to a circle but may be oval, non-symmetrical, a polygon or the like. Besides, the hub 218 includes a first part 220 connected to the connector 16, and a second part 222 provided at a distal end of the first part 220.

As shown in FIG. 16A, the second part 222 is formed in a hollow cylindrical shape. In addition, the second part 222 includes a protruding portion 224 protruding from a distal end surface 220a of the first part 220 along the distal direction of the shaft section 12, and a stopper portion 226 projected from a distal end of the protruding portion 224 toward the shaft section 12 side. The second part 222 is surrounding part of the shaft section 12.

An outer circumferential surface of the first part 220 and an outer circumferential surface of the protruding portion 224 are integrally connected with each other, to form an outer circumferential surface of the hub 218. In addition, the protruding portion 224 is formed with a pair of slits 228, 228 extending in the axial direction of the shaft section 12 (see FIGS. 14 and 15). These slits 228, 228 are opposite to each other, with the axis of the shaft section 12 therebetween. In other words, these slits 228, 228 are disposed at equal intervals along a circumferential direction of the protruding portion 224.

One end portion of each slit 228 reaches the distal end of the protruding portion 224. On the other hand, the other end portion of each slit 228 is rounded, and is located near a rear end of the protruding portion 224. The width of each slit 228 is set to be about one third of the diameter of the shaft section 12. Incidentally, the length and width of the slit 228 can be set arbitrarily.

The stopper portion 226 and the shaft section 12 are spaced from each other, and the spacing is set to be smaller than the thickness of the distal end of the strain relief section 200. In addition, an outer surface of a distal portion of the stopper portion 226 is formed with a tapered surface 226a which decreases in width toward the shaft section 12.

The distal end surface 220a of the first part 220 and an inner surface of the stopper portion 226 terminate at an inner circumferential surface of the protruding portion 224. As a result, a storage chamber 230 is defined by the distal end surface 220a of the first part 220, the inner circumferential surface of the protruding portion 224, and the inner surface of the stopper portion 226. The storage chamber 230 communicates with the through-hole 208, and is opening to the distal side with respect to the shaft section 12. Incidentally, the storage chamber 230 is set to have such a size that the strain relief section 200 in a contracted state can be stored therein.

According to this embodiment, it is possible, by the stopper portion 226 formed with the tapered surface 226a, to suitably prevent the rear end portion of the strain relief section 200 from coming out of the storage chamber 230. As a result, it is possible to prevent the strain relief section 200 and the hub 218 from being separated from each other. In other words, the stopper portion 226 functions as a disengagement-inhibiting mechanism.

According to the catheter 10I in this embodiment, when the strain relief section 200 is drawn toward the connector 16 side, the strain relief section 200 makes contact with the tapered surface 226a of the stopper portion 226, and the stopper portion 226 is pressed outward in the radial direction of the shaft section 12.

When the stopper portion 226 is pressed outward in the radial direction of the shaft section 12, the slits 228, 228 in the protruding portion 224 are enlarged in width, and the stopper portion 226 is displaced outward in the radial direction of the shaft section 12. In other words, the area of the opening of the storage chamber 230 is enlarged. In this instance, incidentally, the strain relief section 200 receives a reaction force from the stopper portion 226, so that the strain relief section 200 is slightly elastically deformed (contracted) inward in the radial direction of the shaft section 12. Then, the strain relief section 200 drawn toward the connector 16 side is guided into the storage chamber 230 via the enlarged opening.

The strain relief section 200 guided into the storage chamber 230 makes contact with the distal end surface 220a of the first part 220, as shown in FIG. 16B, thereby being brought into a contracted state wherein the spacing between adjacent spiral turns of the belt body 220a has been reduced. As a result, the strain relief section 200 is put into a compact state of being stored in the storage chamber 230.

According to the catheter 10I of this embodiment, therefore, it is possible to cope with, for example, a catheter such that the length of the hub 218 cannot be set sufficiently large in relation to the length (the length in the axial direction of the shaft section 12) of the strain relief section 200 of the catheter 10I in the initial state.

In addition, the strain relief section 200 stored in the storage chamber 230 is in the contracted state and, therefore, tends to return to the original state (tends to extend) by its restoring force (spring action). Since the distal end of the strain relief section 200 is locked on the stopper portion 226, however, the strain relief section 200 can be suitably inhibited from coming out through the opening of the storage chamber 230 to the exterior.

In this embodiment, the protruding portion 224 is not restricted to the configuration of being formed with the pair of slits 228, 228. For instance, the protruding portion 224 may be formed with three or more slits 228. Incidentally, in this case, the slits 228 can be arranged at regular intervals along the circumferential direction of the protruding portion 224. This ensures that the opening of the storage chamber 230 can be enlarged in a well-balanced manner.

Now, a guiding catheter 10J (hereinafter referred to also as "catheter 10J") according to a tenth embodiment of the presently disclosed subject matter will be described below, referring to FIG. 17. Incidentally, the catheter 10J in the tenth embodiment can have the same configurations as those of the catheter 10I in the ninth embodiment and the same reference symbols as used above can be used, and detailed description thereof will be omitted. In addition, in FIG. 17, the numerals and graduations on the shaft section 12 as above-mentioned are omitted from drawing (see FIG. 12B), but in practice, the numerals and graduations can be presented on the shaft section 12.

Figure 17:
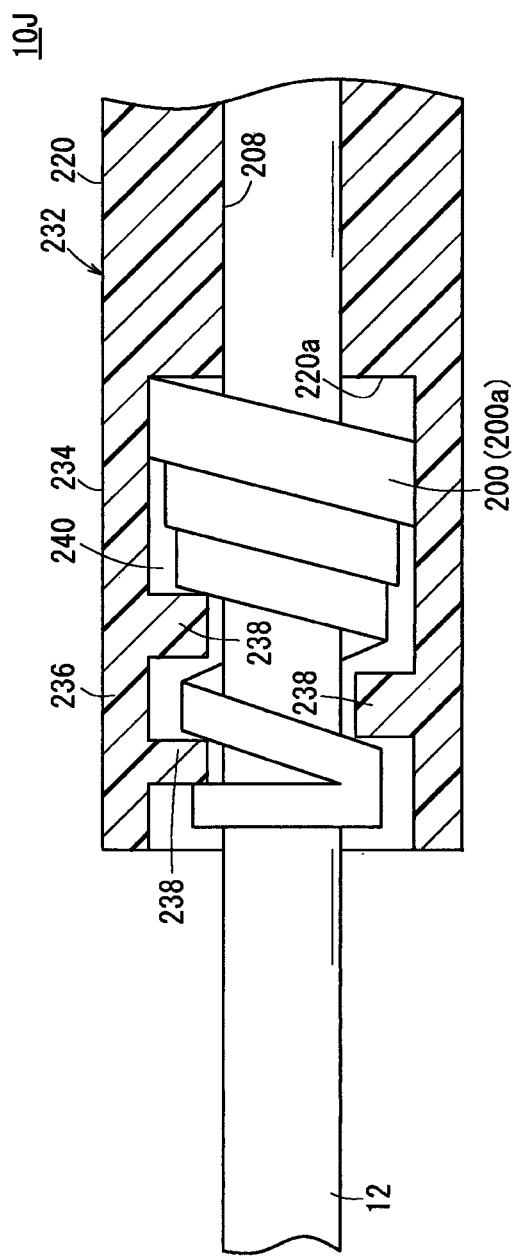
FIG. 17 is a partial enlarged sectional view of a shaft section, a hub, and a strain relief section of a guiding catheter according to a tenth embodiment of the presently disclosed subject matter.

As shown in FIG. 17, this catheter 10J differs from the catheter 10I of the ninth embodiment with respect to a configuration of a second part 234 of a hub 232. Specifically, the second part 234 is formed in a hollow cylindrical shape, and has a protruding portion 236 protruding from the distal end surface 220a of the first part 220 along the distal direction of the shaft section 12, but the stopper portion 226 in the ninth embodiment is omitted. An inner circumferential surface of the protruding portion 236 is formed, at a position somewhat near a distal end, with a spiral projection 238.

The projection 238 extends around the shaft section 12 one time. The spacing between a starting end and a finishing end of the projection 238 is set to be slightly smaller than the width of the proximal portion of the strain relief section 200. The projection 238 and the shaft section 12 are spaced from each other, and the spacing is set to be smaller than the thickness of the distal end of the strain relief section 200.

That surface of the projection 238 which is opposed to the distal end surface 220a of the first part 220 and the distal end surface 220a of the first part 220 terminate at the inner circumferential surface of the protruding portion 236. As a result, a storage chamber 240 is defined by the distal end surface 220a of the first part 220, the opposed surface of the projection 238, and the inner circumferential surface of the protruding portion 236. The storage chamber 240 communicates with the through-hole 208, and is opening to the distal side with respect to the shaft section 12.

According to the catheter 10J of this embodiment, for example, by rotating the strain relief section 200 counterclockwise while gripping the hub 232, the operator can advance the strain relief section 200 into the storage chamber 240. The strain relief section 200 advanced into the storage chamber 240 comes to abut on the distal end surface 220a of the first part 220, to be thereby contracted. This makes it possible to store the strain relief section 200 into the storage chamber 240 in a compact state, and to arbitrarily set the amount of extension of the effective length of the shaft section 12 by regulating the amount of rotation of the strain relief section 200.

In the third to tenth embodiments, the strain relief section 36, 38, 50, 80, 108, 200 may be formed with at least either one of the inside groove 28 and the outside groove 30 described in the first embodiment, or may be formed in a hollow shape like the strain relief section 32 in the second embodiment. This ensures that the anti-kinking property can be suitably exhibited at the proximal-side portion of the shaft section 12, 78 even in the condition where the strain relief section 36, 38, 50, 80, 108, 200 is contracted.

In addition, in the first to tenth embodiments, the strain relief section 18, 32, 36, 38, 50, 80, 108, 200 may be formed by spirally winding a constant-width belt body 18a, 32a, 36a, 38a, 50a, 80a, 108a, 200a around the shaft section 12, 78. In this case, also, the shape of the distalmost end of the belt body 18a, 32a, 36a, 38a, 50a, 80a, 108a, 200a is not particularly restricted. However, the shape can be an annular shape (closed ring). This ensures that the strain relief section 18, 32, 36, 38, 50, 80, 108, 200 can be suitably prevented from being disengaged from the shaft section 12, 78 when contracted (stretched).

Now, a guiding catheter 10K (hereinafter referred to also as "catheter 10K") according to an eleventh embodiment of the presently disclosed subject matter will be described below, referring to FIGS. 18 to 21. Incidentally, certain structures of the catheter 10K in the eleventh embodiment can have the same configuration as those of the catheter 10A in the first embodiment above and are denoted by the same reference symbols as used above, and detailed description of them will be omitted.

Figure 18:
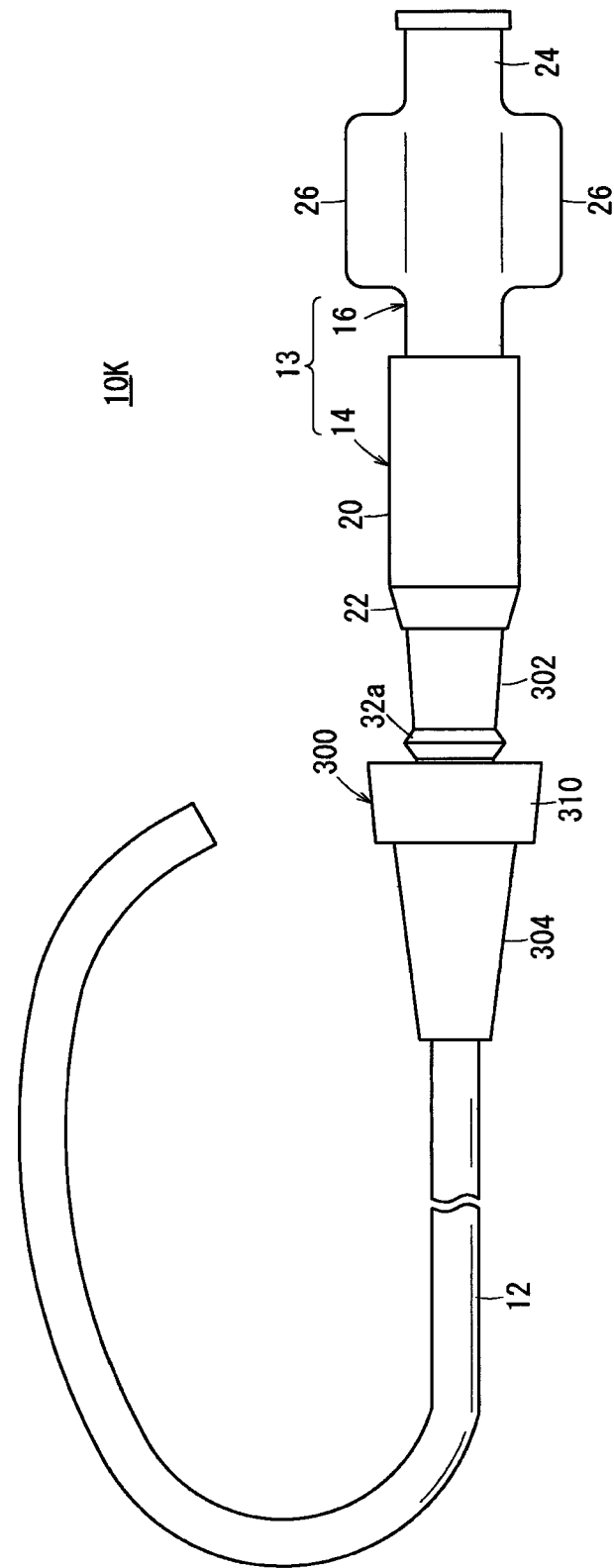
FIG. 18 is a general configuration view of a guiding catheter according to an eleventh embodiment of the presently disclosed subject matter.

As shown in FIG. 18, this catheter 10K differs from the catheter 10A of the first embodiment in configuration of a strain relief section 300. In this embodiment, the range in which the strain relief section 300 surrounds the shaft section 12 is set to be 12 cm, for example.

The strain relief section 300 includes a first member 302 fixed to a distal end of the tapered section 22, and a second member 304 disposed on the first member 302 in a state of being located on the distal side of the first member 302.

Figure 19A:
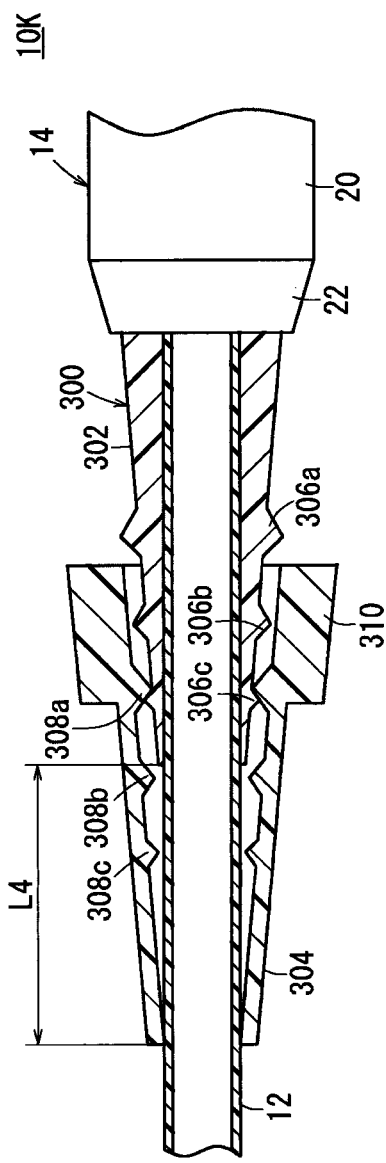
FIG. 19A is a partial enlarged sectional view showing an initial state of the guiding catheter.

As shown in FIG. 19A, the first member 302 is configured in a hollow cylindrical shape, and is gradually tapered off along the distal direction of the shaft section 12. This results in that the first member 302 is lower in rigidity than the hub 14. Incidentally, an inner circumferential surface of the first member 302 is in contact with the outer circumferential surface of the shaft section 12.

An outer circumferential surface of the first member 302 is formed, at predetermined parts located in an area ranging from a roughly middle portion thereof toward the distal side, with a first outside projection 306a, a second outside projection 306b located on the distal side of the first outside projection 306a, and a third outside projection 306c located on the distal side of the second outside projection 306b, in a mutually spaced state. Incidentally, the first to third outside projections 306a to 306c are formed in an annular shape at the outer circumferential surface of the first member 302.

While the spacing between the first outside projection 306a and the second outside projection 306b and the spacing between the second outside projection 306b and the third outside projection 306c can be set arbitrarily, these spacings are set to be roughly equal.

Each of the first to third outside projections 306a to 306c is formed to be triangular in sectional shape. In addition, the sectional area of the second outside projection 306b is set smaller than the sectional area of the first outside projection 306a, and the sectional area of the third outside projection 306c is set smaller than the sectional area of the second outside projection 306b.

The second member 304 is configured in a hollow cylindrical shape, and is gradually tapered off along the distal direction of the shaft section 12. As a result, the second member 304 is lower than the hub 14 in rigidity.

In addition, the second member 304 is so configured that its inside diameter gradually increases toward the hub 14 side. In other words, an inner circumferential surface of the second member 304 is formed in a tapered shape. Incidentally, the taper angle of the inner circumferential surface of the second member 304 and the taper angle of the outer circumferential surface of the first member 302 are set to be roughly equal.

Besides, the second member 304 is so disposed that its distal portion makes contact with the outer circumferential surface of the shaft section 12 and that its proximal portion surrounds a predetermined distal-side range of the first member 302. In short, a distal end of the second member 304 protrudes distally beyond a distal end of the first member 302.

The amount of protrusion, L4, of the second member 304 relative to the first member 302, in other words, the distance from the distal end of the first member 302 to the distal end of the second member 304, can be set arbitrarily. For example, it is set to be 5 cm.

Figure 19B:
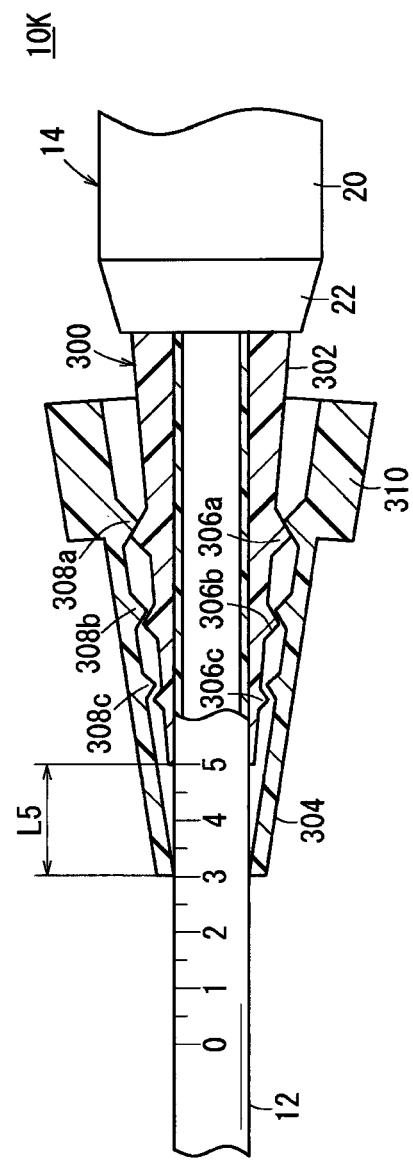
FIG. 19B is a partial enlarged sectional view showing a state in which the amount of protrusion of a second member relative to a first member is reduced.

As shown in FIG. 19B, on that part of the outer circumferential surface of the shaft section 12 which is surrounded only by the second member 304, predetermined numerals and graduations are presented as indication means. In the catheter 10K according to this embodiment, graduations are presented at an interval of 1 cm along the axial direction of the shaft section 12, and numerals 0 to 5 are presented correspondingly to the graduations, sequentially toward the hub 14 side. In FIG. 19B, an auxiliary graduation is presented at a meddle position between adjacent graduations. Incidentally, while the graduations (inclusive of auxiliary graduations) are provided in this embodiment as above-mentioned, the graduations naturally may be omitted. In addition, in the case where the numerals are presented in addition to the graduations, the numerals may be omitted, like the graduations.

The inner circumferential surface of the second member 304 is formed, near a middle portion thereof, with a first inside projection 308a, a second inside projection 308b located on the distal side of the first inside projection 308a, and a third inside projection 308c located on the distal side of the second inside projection 308b, in a mutually spaced state. Incidentally, the first to third inside projections 308a to 308c are formed in an annular shape at the inner circumferential surface of the second member 304.

The spacing between the first inside projection 308a and the second inside projection 308b is set to be equal to the spacing between the first outside projection 306a and the second outside projection 306b. In addition, the spacing between the second inside projection 308b and the third inside projection 308c is set to be equal to the spacing between the second outside projection 306b and the third outside projection 306c. Incidentally, the spacing between the first inside projection 308a and the second inside projection 308b and the spacing between the second inside projection 308b and the third inside projection 308c can be set arbitrarily.

Each of the first to third inside projections 308a to 308c is formed to be roughly triangular in sectional shape. Besides, the sectional area of the first inside projection 308a is set equal to the sectional area of the first outside projection 306a; the sectional area of the second inside projection 308b is set equal to the sectional area of the second outside projection 306b; and the sectional area of the third inside projection 308c is set equal to the sectional area of the third outside projection 306c.

At that part of the outer circumferential surface of the second member 304 which is located at a rear end, a projection 310 projecting outward in the radial direction of the shaft section 12 is formed in an annular shape.

In this embodiment, in an initial state of the catheter 10K, that surface (distal end surface) of the first inside projection 308a which is located on the distal side is in contact with that surface (rear end surface) of the third outside projection 306c which is located on the rear end side.

According to the catheter 10K in this embodiment, when the operator draws the second member 304 toward the hub 14 side while hooking a finger on the projection 310, the distal end surface of the first inside projection 308a is separated from the rear end surface of the third outside projection 306c, and a rear end surface of the first inside projection 308a makes contact with a distal end surface of the second outside projection 306b. Thus, the second member 304 is displaced toward the hub 14 side in relation to the first member 302. In other words, the amount of protrusion, L4, of the second member 304 relative to the first member 302 is reduced.

Subsequently, with the second member 304 drawn further, the second member 304 is forced open by the second outside projection 306b outward in the radial direction of the shaft section 12. As a result, the inside diameter of the second member 304 is enlarged, whereby the first inside projection 308a is made to come over the second outside projection 306b.

Then, for example, when the second member 304 is drawn until the distal end surface of the first inside projection 308a makes contact with a rear end surface of the first outside projection 306a, the distal end of the second member 304 is located in the vicinity of the graduation of 3 cm presented on the outer circumferential surface of the shaft section 12 (see FIG. 19B). In short, the amount of protrusion, L4, of the second member 304 is reduced (to an amount of protrusion, L5), and the effective length of the shaft section 12 is enlarged by about 3 cm.

Incidentally, in this condition, the distal end surface of the first inside projection 308a is in contact with the rear end surface of the first outside projection 306a, so that displacement of the second member 304 relative to the first member 302 can be restrained to an appropriate extent. This makes it possible to maintain the condition where the effective length of the shaft section 12 is enlarged.

In this embodiment, the first and second members 302 and 304 are tapered off along the distal direction of the shaft section 12; therefore, the flexibility of the shaft section 12 can be enhanced along the direction from the proximal portion toward the distal end of the shaft section 12. This ensures that the anti-kinking property can be suitably exhibited at the proximal-side portion of the shaft section 12.

Further, in this embodiment, the projection 310 is disposed at the outer circumferential surface of the second member 304, so that an operation of sliding the second member 304 can be carried out easily.

In this embodiment, the sectional shape of the first to third outside projections 306a to 306c and the first to third inside projections 308a to 308c is not limited to a roughly triangular sectional shape; for example, a roughly rectangular sectional shape or a roughly semicircular sectional shape may also be adopted.

In addition, the first to third outside projections 306a to 306c may not necessarily be formed in an annular shape at the outer circumferential surface of the first member 302. For instance, the first to third outside projections 306a to 306c may be formed in such a size as to extend around the first member 302 by one half or one quarter of the circumference. The sectional area of each of the first to third outside projections 306a to 306c may be set arbitrarily.

Furthermore, the first to third inside projections 308a to 308c may not necessarily be formed in an annular shape at the inner circumferential surface of the second member 304. For example, the first to third inside projections 308a to 308c may be formed in such a size as to extend along the inner circumferential surface of the second member 304 by one half or one quarter of the circumference. The sectional area of each of the first to third inside projections 308a to 308c may be set arbitrarily.

The number of the outside projections 306 can be set arbitrarily. The number of the outside projection(s) 306 may be one, two, or four or more. The same applies to the inside projection(s) 308, as well.

In this embodiment, the projection 310 may not necessarily be formed in an annular shape at the outer circumferential surface of the second member 304. The shape of the projection 310 can be set arbitrarily, insofar as the projection 310 is projected from the outer circumferential surface of the second member 304 to such an extent that an operator's finger can be hooked on the projection 310.

In this embodiment, the numerals presented on the outer circumferential surface of the shaft section 12 may be numerals corresponding to the distance from the distal end of the shaft section 12 to the distal end of the strain relief section 300. In this case, the effective length of the shaft section 12 that has been enlarged can be easily grasped. In addition, the graduations and numerals may be presented on the outer circumferential surface of the first member 302. In this case, also, the amount of extension of the effective length of the shaft section 12 and the like can be easily grasped.

In the catheter 10K according to this embodiment, either one group of projections of the first to third outside projections 306a to 306c and the first to third inside projections 308a to 308c may be omitted. In addition, in this embodiment, the projection 310 may be omitted.

Figure 20:
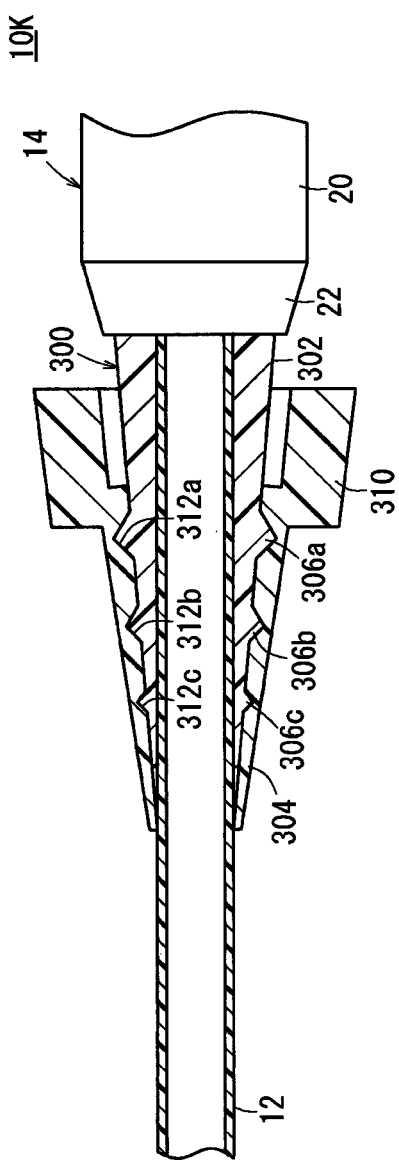
FIG. 20 is a partial enlarged sectional view showing a first modification of the guiding catheter according to the eleventh embodiment of the presently disclosed subject matter.

Now, a first modification of this embodiment will be described below, referring to FIG. 20. In this modification, as shown in FIG. 20, in place of the first to third inside projections 308a to 308c, first to third inside recesses 312a to 312c are formed in the inner circumferential surface of the second member 304.

Each of the first to third inside recesses 312a to 312c is formed in an annular shape in the inner circumferential surface of the second member 304. In addition, the shape of the first inside recess 312a corresponds to the shape of the first outside projection 306a, the shape of the second inside recess 312b corresponds to the shape of the second outside projection 306b, and the shape of the third inside recess 312c corresponds to the shape of the third outside projection 306c. Incidentally, the shape of the first to third inside recesses 312a to 312c, and the like can be set arbitrarily.

According to this modification, the first to third outside projections 306a to 306c can each be engaged with at least one of the first to third inside recesses 312a to 312c, so that displacement of the second member 304 relative to the first member 302 can be restrained to an appropriate extent.

Figure 21:
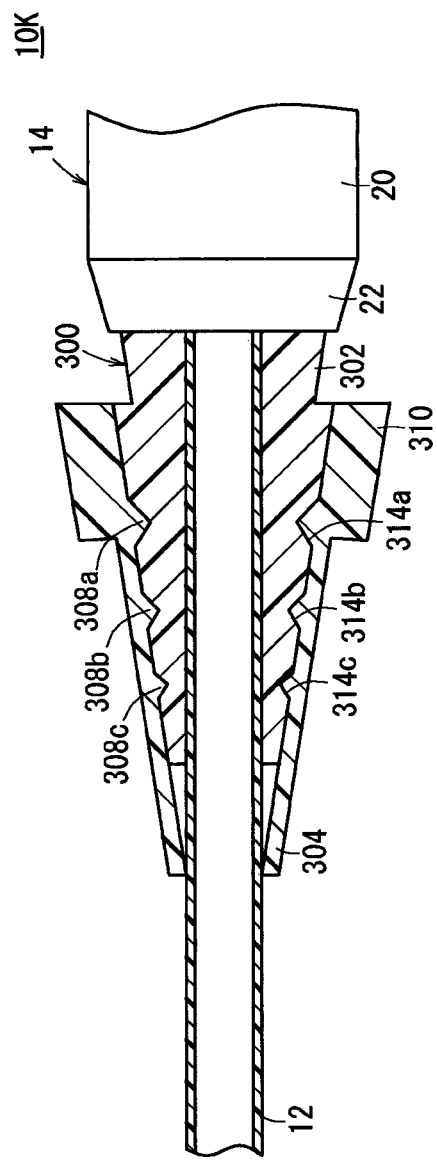
FIG. 21 is a partial enlarged sectional view showing a second modification of the guiding catheter according to the eleventh embodiment of the presently disclosed subject matter.

Now, a second modification of this embodiment will be described below, referring to FIG. 21. In this modification, as shown in FIG. 21, in place of the first to third outside projections 306a to 306c, first to third outside recesses 314a to 314c are formed in the outer circumferential surface of the first member 302.

Each of the first to third outside recesses 314a to 314c is formed in an annular shape in the outer circumferential surface of the first member 302. In addition, the shape of the first outside recess 314a corresponds to the shape of the first inside projection 308a, the shape of the second outside recess 314b corresponds to the shape of the second inside projection 308b, and the shape of the third outside recess 314c corresponds to the shape of the third inside projection 308c. Incidentally, the shape of the first to third outside recesses 314a to 314c, and the like can be set arbitrarily.

According to this modification, the first to third inside projections 308a to 308c can each be engaged with at least one of the first to third outside recesses 314a to 314c; therefore, displacement of the second member 304 relative to the first member 302 can be restrained to an appropriate extent.

Now, a guiding catheter 10L (hereinafter referred to also as "catheter 10L") according to a twelfth embodiment of the presently disclosed subject matter will be described below, referring to FIGS. 22A and 22B. Incidentally, in the catheter 10L of the twelfth embodiment, structures having the same configurations as those of the catheter 10K in the eleventh embodiment are denoted by the same reference symbols as used above, and detailed descriptions of them will be omitted. The same applies also in the thirteenth to sixteenth embodiments which will be described later.

As shown in FIG. 22A, this catheter 10L differs from the catheter 10K of the eleventh embodiment with respect to the configuration of strain relief section 316. Specifically, an outer circumferential surface of a first member 318 is formed with a first screw part 320, and an inner circumferential surface of a second member 322 is formed with a second screw part 324 for screw engagement with the first screw part 320. Incidentally, the first to third outside projections 306a to 306c, the first to third inside projections 308a to 308c, and the projection 310 in the eleventh embodiment are omitted.

According to the catheter 10L in this embodiment, for example, as shown in FIG. 22B, by rotating the second member 322 counterclockwise as viewed from the proximal side of the catheter 10L, the second member 322 can be displaced toward the hub 14 side in relation to the first member 318. As a result, the amount of protrusion of the second member 322 relative to the first member 318 is reduced, so that the effective length of the shaft section 12 can be enlarged.

In addition, by regulating the amount of rotation of the second member 322, the amount of protrusion of the second member 322 relative to the first member 318 can be set arbitrarily.

Figure 24:
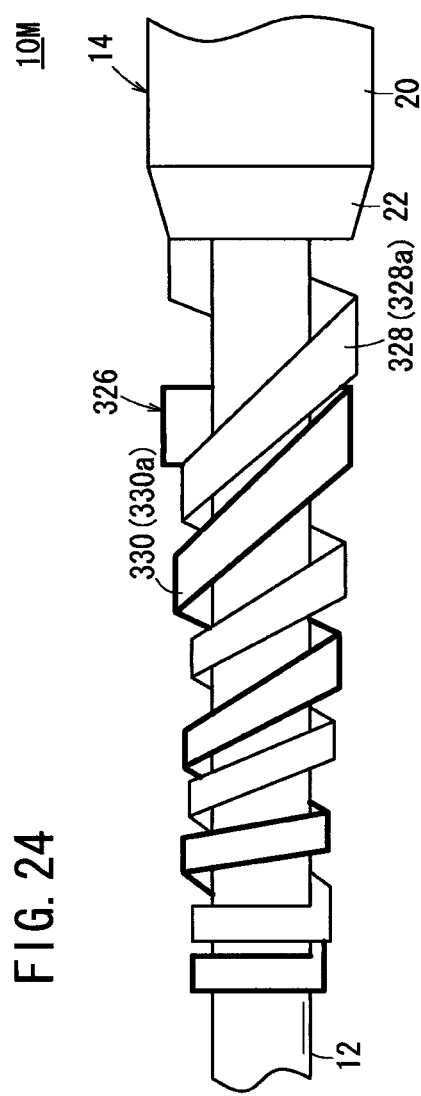
FIG. 24 is a partial enlarged lateral view showing a modification of the guiding catheter according to the thirteenth embodiment of the presently disclosed subject matter.

Now, a guiding catheter 10M (hereinafter referred to also as "catheter 10M") according to a thirteenth embodiment of the presently disclosed subject matter will be described below, referring to FIGS. 23A to 24. In FIGS. 23A to 24, the numerals and graduations on the shaft section 12 as above-mentioned (see FIG. 19B) are omitted from the drawing; in practice, however, the numerals and graduations can be presented on the shaft section 12. In addition, in FIGS. 23A to 24, for distinction between a first member 328 and a second member 330 which will be described later, the first member 328 is drawn in thin lines whereas the second member 330 is drawn in thick lines.

As shown in FIG. 23A, this catheter 10M differs from the catheter 10K of the eleventh embodiment with respect to the configuration of strain relief section 326. Specifically, the first member 328 is formed by spirally winding a belt body 328a around the shaft section 12 clockwise as viewed from the proximal side of the catheter 10M, a plurality of times (in this embodiment, four times). The interval (pitch) between adjacent spiral turns of the belt body 328a is substantially constant. It is to be noted here, however, that the interval may vary. The first member 328 (the belt body 328a) is gradually decreased in width and in thickness along the distal direction of the shaft section 12.

Here, the shape of a distalmost end of the first member 328 is not particularly restricted; however, it can be an annular shape (closed ring). This shape ensures that the first member 328 can be suitably prevented from being disengaged from the shaft section 12.

The second member 330 is formed by spirally winding a belt body 330a around the shaft section 12 counterclockwise as viewed from the proximal side of the catheter 10M, a plurality of times (in this embodiment, four times). In other points of configuration, the second member 330 can be the same as the above-mentioned first member 328.

According to the catheter 10M in this embodiment, as shown in FIG. 23B, when the second member 330 is drawn toward the hub 14 side while rotating it counterclockwise (or clockwise) as viewed from the proximal side of the catheter 10M, the second member 330 is displaced toward the hub 14 side relative to the first member 328 while the spiral of the second member 330 comes over the spiral of the first member 328. As a result, the amount of protrusion of the second member 330 relative to the first member 328 is reduced, so that the effective length of the shaft section 12 can be enlarged.

In addition, when the effective length of the shaft section 12 is enlarged, the spiral of the first member 328 and the spiral of the second member 330 are in contact with each other in an intersecting state. This structure ensures that displacement of the second member 330 relative to the first member 328 can be restrained to an appropriate extent by frictional forces at the intersecting parts.

Further, in this embodiment, the first and second members 328 and 330 are each formed in a spiral shape. This ensures that the strain relief section 326 is bent more easily, as compared with a case where the first and second members 328 and 330 are each formed in a hollow cylindrical shape. This enables the anti-kinking property to be suitably exhibited at the proximal-side portion of the shaft section 12.

Furthermore, the first and second members 328 and 330 are each gradually decreased in width and in thickness along the distal direction of the shaft section 12; therefore, the flexibility of the shaft section 12 can be enhanced along the direction from the proximal portion toward the distal end of the shaft section 12. This enables the anti-kinking property to be suitably exhibited at the proximal-side portion of the shaft section 12.

In this embodiment, as shown in FIG. 24, the winding direction of the spiral of the second member 330 may be the same as the winding direction of the spiral of the first member 328. In this case, by rotating the second member 330 counterclockwise as viewed from the proximal side of the catheter 10M, the second member 330 can be displaced toward the hub 14 side relative to the first member 328. Incidentally, a similar effect can be obtained also in a case where the respective winding directions of the spiral of the first and second members 328 and 330 are set to be counterclockwise as viewed from the proximal side of the catheter 10M.

In this embodiment, the numbers of turns of the spiral of the first and second members 328 and 330, the shape of the belt bodies, and the like can be set arbitrarily.

Now, a guiding catheter 10N (hereinafter referred to also as "catheter 10N") according to a fourteenth embodiment of the presently disclosed subject matter will be described below, referring to FIGS. 25A and 25B.

Figure 25A:
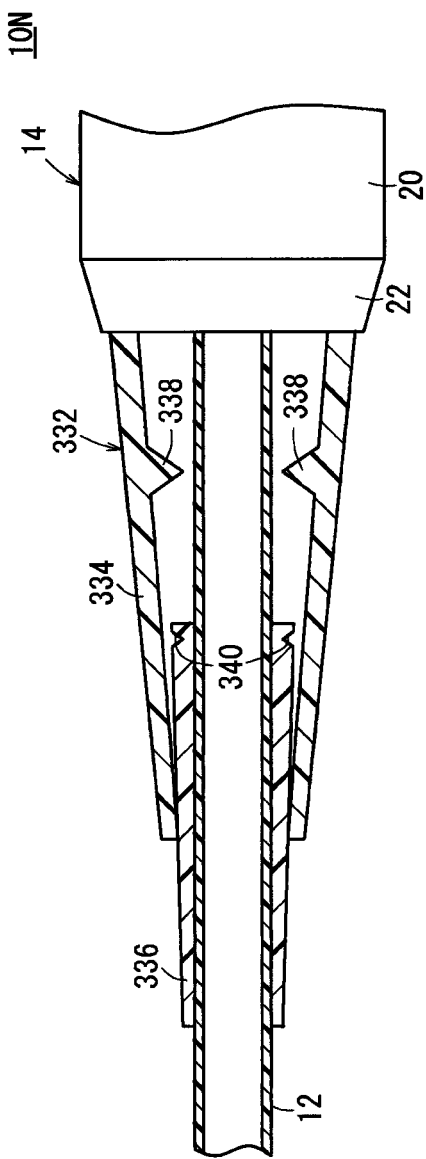
FIG. 25A is a partial enlarged sectional view showing an initial state of the guiding catheter.

As shown in FIG. 25A, this catheter 10N differs from the catheter 10K of the eleventh embodiment with respect to the configuration of strain relief section 332. Specifically, an inner circumferential surface of a first member 334 is not in contact with the shaft section 12. In addition, the first member 334 is surrounding part of a second member 336. At a position slightly on the rear end side of a middle position of the inner circumferential surface of the first member 334, a projection 338 projecting inward in the radial direction of the shaft section 12 is formed in an annular shape. The projection 338 is formed to be roughly triangular in sectional shape.

An inner circumferential surface of the second member 336 is in contact with the outer circumferential surface of the shaft section 12. In the vicinity of a rear end portion of an outer circumferential surface of the second member 336, a recess 340 roughly triangular in sectional shape and capable of engagement with the projection 338 is formed in an annular shape.

Incidentally, the first and second members 334 and 336 are each tapered off along the distal direction of the shaft section 12. In an initial state of the catheter 10N, therefore, the second member 336 is positioned by making contact with the inner circumferential surface of the first member 334, in a state of appropriately protruding in relation to the first member 334.

Figure 25B:
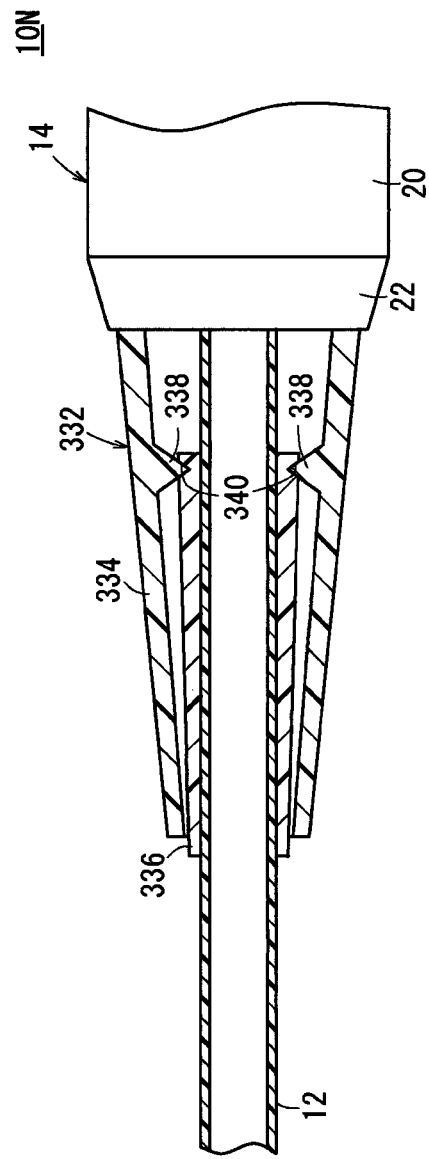
FIG. 25B is a partial enlarged sectional view showing a state in which the amount of protrusion of a second member relative to a first member is reduced.

According to the catheter 10N in this embodiment, as shown in FIG. 25B, when the second member 336 is drawn toward the hub 14 side, the second member 336 is inserted into a space between the first member 334 and the shaft section 12, so that the amount of protrusion of the second member 336 relative to the first member 334 can be reduced. This makes it possible to extend the effective length of the shaft section 12.

In addition, the projection 338 is engaged with the recess 340 at a stage where the second member 336 has been drawn to a certain extent. Therefore, displacement of the second member 336 in the axial direction of the shaft section 12 can be restrained to an appropriate extent. This makes it possible to maintain a state wherein the effective length of the shaft section 12 has been enlarged. Further, it is possible to obviate or prevent a situation in which the second member 336 entering the space between the first member 334 and the shaft section 12 might not be able to be taken out.

In this embodiment, the shapes of the projection 338 and the recess 340, and the like can be set arbitrarily. Besides, the projection 338 and the recess 340 may be omitted. Further, the numerals and graduations presented on the outer circumferential surface of the shaft section 12 may be presented on the outer circumferential surface of the second member 336. In this case, also, the amount of extension of the effective length of the shaft section 12 can be easily grasped or understood.

Now, a guiding catheter 10O (hereinafter referred to also as "catheter 10O") according to a fifteenth embodiment of the presently disclosed subject matter will be described below, referring to FIGS. 26A and 26B.

As shown in FIG. 26A, this catheter 10O differs from the catheter 10K of the eleventh embodiment with respect to the configuration of strain relief section 342. An outer circumferential surface of a first member 344 is formed, in an area ranging from a position near a distal end to a slightly rear side of a middle portion, with a groove 346. A groove bottom surface of the groove 346 is provided, at an end portion on the distal side with respect to the shaft section 12, with a projection 348 which is roughly triangular in sectional shape. In addition, a distal end surface of the projection 348 is continuous with groove side surfaces of the groove 346. As a result, an engagement hole 350 roughly triangular in sectional shape is defined by the distal end surface of the projection 348 and the groove side surfaces of the groove 346.

An inner circumferential surface of a second member 352 is in contact with the outer circumferential surface of the shaft section 12. Besides, in a rear end surface of the second member 352, a hole 354 is formed which corresponds to the shape on the distal side (inclusive of a distal portion) of the first member 344. Roughly in the center of the hole 354, the shaft section 12 is located. As a result, the hole 354 is formed in an annular shape. In addition, the hole 354 is decreased in width along the distal direction of the shaft section 12. At an end on the hub 14 side, of wall surfaces of the hole 354, a stopper portion 356 is provided which has a shape corresponding to the shape of the engagement hole 350.

In the catheter 10O of this embodiment, in an initial state, the stopper portion 356 is disposed in the engagement hole 350. As a result, the second member 352 is positioned in a state of protruding in an appropriate extent relative to the first member 344. Therefore, it is possible, for example, to suitably obviate a situation in which during an operation of the catheter 10O, the second member 352 might be displaced along the distal direction of the shaft section 12 in relation to the first member 344, to be separated from the first member 344.

According to the catheter 10O in this embodiment, when the second member 352 is drawn toward the hub 14 side, the stopper portion 356 comes over the projection 348, and the second member 352 is displaced toward the hub 14 side while a distal-side portion of the first member 344 is inserted into the hole 354. As a result, the amount of protrusion of the second member 352 relative to the first member 344 can be reduced, so that the effective length of the shaft section 12 can be enlarged. Incidentally, in this instance, the stopper portion 356 is located in the groove 346 and, therefore, would not obstruct the displacement operation of the second member 352.

In this embodiment, a recess or projection capable of engagement with the stopper portion 356, in the condition wherein the second member 352 has been displaced toward the hub 14 side, may further be provided. In this case, it is possible to suitably maintain a condition wherein the amount of protrusion of the second member 352 relative to the first member 344 has been reduced.

In this embodiment, the shapes of the groove 346 and the stopper portion 356, and the like can be set arbitrarily. In addition, the groove 346 and the stopper portion 356 may be omitted. Further, the numerals and graduations presented on the outer circumferential surface of the shaft section 12 may be presented on an outer circumferential surface of the second member 352. In this case, the amount of extension of the effective length of the shaft section 12 can be easily grasped or understood.

Now, a guiding catheter 10P (hereinafter referred to also as "catheter 10P") according to a sixteenth embodiment of the presently disclosed subject matter will be described below, referring to FIGS. 27A and 27B.

As shown in FIG. 27A, this catheter 10P differs from the catheter 10K of the eleventh embodiment with respect to the configuration of a strain relief section 358. Specifically, a first member 360 is not in contact with the shaft section 12. In addition, an outer circumferential surface of the first member 360 is formed with a first screw part 362 in a predetermined distal-side region thereof.

An inner circumferential surface of a second member 364 is in contact with the outer circumferential surface of the shaft section 12. In a rear end surface of the second member 364, an annular hole 366 can be formed which has a shape corresponding to the shape on the distal side (inclusive of a distal portion) of the first member 360.

The annular hole 366 is decreased in width along the distal direction of the shaft section 12. The hole depth of the annular hole 366 can be set arbitrarily; for example, the depth is set to be about one half of the length of the first member 360 as measured along the axial direction of the shaft section 12. In addition, at a wall surface forming an outer circumferential portion of the annular hole 366, a second screw part 368 is formed which is screw engaged with the first screw part 362. Incidentally, a wall portion forming an inner circumferential portion of the annular hole 366 is surrounding part of the shaft section 12.

According to the catheter 10P in this embodiment, as shown in FIG. 27B, for example, by rotating the second member 364 counterclockwise as viewed from the proximal side of the catheter 10P, the second member 364 can be displaced toward the hub 14 side relative to the first member 360. As a result, the amount of protrusion of the second member 364 relative to the first member 360 is reduced, so that the effective length of the shaft section 12 can be enlarged.

By regulating the amount of rotation of the second member 364, the amount of protrusion of the second member 364 relative to the first member 360 can be set arbitrarily.

In this embodiment, a configuration may be adopted wherein either one of the first and second screw parts 362 and 368 is replaced by a projection(s), and the other of the first and second screw parts 362 and 368 is replaced by a projection(s) or recess(es) for engagement with the projection(s). In this case, a similar effect to that of the eleventh embodiment mentioned above can be obtained.

The presently disclosed subject matter is not restricted to the above-described embodiments, and various configurations naturally can be adopted within the scope of the gist of the presently disclosed subject matter.

The presently disclosed subject matter is applicable to a variety of catheters, examples of which include a balloon catheter and an angiography catheter which are to be inserted directly into a guiding catheter, and a main catheter and a sub-catheter to be inserted into a guiding catheter through a Y-connector.

It will be apparent to those skilled in the art that various modifications and variations can be made in the presently disclosed subject matter without departing from the spirit or scope of the presently disclosed subject matter. Thus, it is intended that the presently disclosed subject matter cover the modifications and variations of the presently disclosed subject matter provided they come within the scope of the appended claims and their equivalents. All related art references described above are hereby incorporated in their entirety by reference.

What is claimed is:

1. A catheter comprising:
a flexible shaft having a proximal portion and a distal portion opposed to the proximal portion along a longitudinal axis;
a hub disposed at the proximal portion of the shaft; and
a strain relief surrounding a predetermined proximal-side range of the shaft and including a distal end and a proximal end, and the distal end being closer to the distal portion of the shaft than the proximal end, wherein
the distal end of the strain relief is configured such that the distal end of the strain relief is movable to be displaced along an axial direction of the shaft towards the proximal portion where the hub is located,
the hub includes a storage chamber in which at least part of the strain relief is configured to be stored when the distal end of the strain relief is displaced along the axial direction of shaft,
the storage chamber is opening to the distal side with respect to the shaft,
the strain relief is spirally wound around the shaft, and
the storage chamber includes a spiral-shaped groove configured to engage with the strain relief.

2. The catheter according to claim 1, wherein the strain relief is configured to contract in the axial direction of the shaft.

3. A catheter comprising:
a flexible shaft having a proximal portion and a distal portion opposed to the proximal portion along a longitudinal axis;
a hub disposed at the proximal portion of the shaft; and
a strain relief surrounding a predetermined proximal-side range of the shaft and including a distal end and a proximal end, and the distal end being closer to the distal portion of the shaft than the proximal end, wherein
the distal end of the strain relief is configured such that the distal end of the strain relief is moveable to be displaced along an axial direction of the shaft towards the proximal portion where the hub is located,
the strain relief is configured to contract in the axial direction of the shaft,
the strain relief is configured in a belt-like shape and is spirally wound around the shaft,
the strain relief comprises at least two spiral turns, wherein at least one of the spiral turns is configured to be disposed beneath a spiral turn located on the most proximal side of the flexible shaft; and
wherein a spacing between the flexible shaft and an inner surface of the spiral turn located on the most proximal side of the flexible shaft is wider than a spacing between the flexible shaft and an outer surface of the spiral turn located on the distal side of the flexible shaft.

4. The catheter according to claim 3, wherein at least one of an outer circumferential surface and an inner circumferential surface of the strain relief includes a groove.

5. The catheter according to claim 2, wherein at least one of an outer circumferential surface and an inner circumferential surface of the strain relief includes a groove.

6. The catheter according to claim 3, wherein the hub includes a storage chamber in which at least part of the strain relief is configured to be stored when the distal end of the strain relief is displaced along the axial direction of the shaft.

7. The catheter according to claim 6, wherein the
strain relief is spirally wound around the shaft, and
the storage chamber includes a spiral-shaped groove configured to engage with the strain relief.

8. The catheter according to claim 7, wherein the hub is one of fixed and rotatable with respect to the shaft.

9. A catheter comprising:
a flexible shaft having a proximal portion and a distal portion opposed to the proximal portion along a longitudinal axis,
a strain relief surrounding a predetermined proximal-side range of the shaft and including a distal end and a proximal end, and the distal end being closer to the distal portion of the shaft than the proximal end, wherein the distal end of the strain relief is configured such that the distal end of the strain relief is movable to be displaced along an axial direction of the shaft towards the proximal portion where the hub is located, and the strain relief has:
- a first member disposed at a distal end of the hub; and
- a second member protruding along a distal direction of the first member and which is configured to be varied in the amount of protrusion relative to the first member, and wherein the strain relief includes a plurality of projections and recesses that mate with each other when the distal portion of the strain relief is moved relative to the proximal portion of the strain relief;

wherein a surface of the first member which faces the second member includes a first engagement part, and a surface of the second member which faces the first member includes a second engagement part configured to engage with the first engagement part;

wherein the first engagement part is one of the projections and the recesses and the second engagement part is one of the projections and the recesses; and wherein the first and second members are each formed in a belt-like shape and are spirally wound around the shaft.

10. The catheter according to claim 9, wherein the plurality of projections and recesses mate with each other and lock together when the distal portion of the strain relief is moved relative to the proximal portion of the strain relief.

\* \* \* \* \*